(12) United States Patent
Hong et al.

(10) Patent No.: US 9,168,225 B2
(45) Date of Patent: Oct. 27, 2015

(54) NANO-HYBRID DELIVERY SYSTEM FOR SEQUENTIAL UTILIZATION OF PASSIVE AND ACTIVE TARGETING

(75) Inventors: Seungpyo Hong, Naperville, IL (US); Ying Liu, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/642,868

(22) PCT Filed: Apr. 20, 2011

(86) PCT No.: PCT/US2011/033158
§ 371 (c)(1),
(2), (4) Date: Jan. 2, 2013

(87) PCT Pub. No.: WO2011/133617
PCT Pub. Date: Oct. 27, 2011

(65) Prior Publication Data
US 2013/0121918 A1    May 16, 2013

Related U.S. Application Data

(60) Provisional application No. 61/327,200, filed on Apr. 23, 2010.

(51) Int. Cl.
*A61K 9/127* (2006.01)
*A61K 9/51* (2006.01)
*A61K 9/14* (2006.01)

(52) U.S. Cl.
CPC .............. *A61K 9/127* (2013.01); *A61K 9/1273* (2013.01); *A61K 9/14* (2013.01); *A61K 9/5153* (2013.01); *A61K 9/146* (2013.01)

(58) Field of Classification Search
CPC ........................................................ A61K 9/146
See application file for complete search history.

(56) References Cited

U.S. PATENT DOCUMENTS

| | | | |
|---|---|---|---|
| 2009/0061010 A1 | 3/2009 | Zale et al. | 424/501 |
| 2009/0074828 A1 | 3/2009 | Alexis et al. | 424/422 |
| 2010/0266491 A1 | 10/2010 | Farokhzad et al. | 424/1.29 |

FOREIGN PATENT DOCUMENTS

| WO | WO 2006/095936 A1 | 9/2006 |
|---|---|---|
| WO | WO 2009/039502 A1 | 3/2009 |

OTHER PUBLICATIONS

Li, Polymer-drug conjugates: Recent development in clinical oncology, Advanced Drug Delivery Reviews, 2008, 60, 886-898.*
Kim et al. "Physicochemical Characterization of Poly(L-lactic Acid) and Poly(D,L-lactide-co-glycolide) Nanoparticles with Plyethylenimine as Gene Delivery Carrier" International Journal of Pharmaceutics 2005 298:255-262.
Ko at al. "Liposome Encapsulated Polyethylenimine/ODN Polyplexes for Brain Targeting" Journal of Controlled Release 2009 133:230-237.

(Continued)

*Primary Examiner* — Paul Dickinson
(74) *Attorney, Agent, or Firm* — Licata & Tyrrell P.C.

(57) ABSTRACT

The present invention features nanohybrid drug delivery composition which combines both passive and active targeting for the prevention and treatment of disease. The composition is shell-encapsulated multivalent polymeric scaffold with a therapeutic agent and targeting agent attached thereto.

10 Claims, 5 Drawing Sheets

(56) References Cited

OTHER PUBLICATIONS

Matsumura, Y. and Maeda, H. "A New Concept for Macromolecular Therapeutics in Cancer Chemotherapy: Mechanism of Tumoritropic Accumulation of Proteins and the Antitumor Agent Smancs" Cancer Research 1986 46:6387-6392.

Peer et al. "Nanocarriers as an Emerging Platform for Cancer Therapy" Nature Nanotechnology 2007 2:751-760.

Perez et al. "Poly(lactic acid)-poly(ethylene glycol) Nanoparticles as New Carriers for the Delivery of Plasmid DNA" Journal of Controlled Release 2001 75:211-224.

Son, S. and Kim, W. J. "Biodegradable Nanoparticles Modified by Branched Polyethylenimine for Plasmid DNA Delivery" Biomaterials 2010 31:133-143.

Vauthier, C. and Bouchemal, K. "Methods for the Preparation and Manufacture of Polymeric Nanoparticles" Pharmaceutical Research 2009 26(5):1025-1058.

Watanabe et al. "Fluorescent Liposome for Intravital Staining of Kupffer Cells to Aid In Vivo Microscopy in Rats" Methods and Findings in Experimental and Clinical Pharmacology 2007 29(5):321-327.

Yuan et al. "Vascular Permeability in a Human Tumor Xenograft: Molecular Size Dependence and Cutoff Size" Cancer Research 1995 55:3752-3756.

International Search Report from PCT/US2011/033158, Jun. 20, 2011.

International Preliminary Report on Patentability PCT/US2011/033158, Nov. 1, 2012.

\* cited by examiner

NANO-HYBRID DELIVERY SYSTEM FOR SEQUENTIAL UTILIZATION OF PASSIVE AND ACTIVE TARGETING

This application is a U.S. National Stage Application of PCT/US2011/033158 filed Apr. 20, 2011 and claims benefit of priority to U.S. Provisional Application Ser. No. 61/327, 200, filed Apr. 23, 2010, the contents of each of which are incorporated herein by reference in their entirety.

This invention was made with government support under National Science Foundation grant number CBET-0931472. The government has certain rights in this invention.

BACKGROUND OF THE INVENTION

Multifunctional macromolecules have demonstrated great potential as drug delivery vectors (Nori & Kopecek (2005) *Adv. Drug Deliv. Rev.* 57:609-636; Patri, et al. (2002) *Curr. Opin. Chem. Biol.* 6:466-471). In particular, polycationic polymers have been widely explored for many biomedical applications, including gene delivery (Verma & Somia (1997) *Nature* 389:239-242). One of the most commonly used cationic polymers is polyethylenimine (PEI) that has been primarily used as a nonviral gene delivery vector given its capacity to protect DNA from lysosomal degradation and promote endosomal escape (Boussif, et al. (1995) *Proc. Natl. Acad. Sci. USA* 92:7297-7301; Gebhart & Kabanov (2001) *J. Control. Release* 73:401-416; Akinc, et al. (2005) *J. Gene Med.* 7:657-663; Urban-Klein, et al. (2005) *Gene Ther.* 12:461-466). Another characteristic of PEI and other polycations, such as poly(lysine) and poly(amidoamine) (PAMAM) dendrimers, is that they spontaneously interact with biological membranes (Hong, et al. (2009) *Bioconjugate Chem.* 20:1503-1513; Hong, et al. (2004) *Bioconjugate Chem.* 15:774-782). This facilitates their cellular internalization without the need for ligands for receptor-mediated endocytosis or other internalization routes. However, toxicity issues related to the strong cationic surface charge have hindered clinical translation of the polycations in drug delivery, largely due to the lack of kinetic control over non-specific electrostatic interactions with blood components and rapid clearance by the reticuloendothelial system (RES) (Oupicky, et al. (2002) *J. Drug Target.* 10:93-98).

As most of the currently available anti-cancer treatment agents frequently accompany severe side effects through high toxicity to normal cells and tissues, it is highly desirable to home the drug delivery system to the tissue of interest. The passive targeting strategy using nanotechnology has proven to be efficient in reducing the toxic side effects, thereby increasing the therapeutic index of anti-cancer agents (Matsumura & Maeda (1986) *Cancer Res.* 46:6387-6392; Yuan, et al. (1995) *Cancer Res.* 55:3752-3756; Peer, et al. (2007) *Nat. Nanotechnol.* 2:751-760). Passive targeting utilizes the enhanced permeability and retention (EPR) effect that is defined by leaky vasculature and poor lymphatic drainage around tumors, resulting in the accumulation of the nanoscale delivery system at the tumor site. In order to take advantage of the EPR effect, a nanoscale delivery system needs to be in the range of 50-200 nm, which can be achieved using well-established manufacturing techniques (Couvreur & Vauthier (2006) *Pharm. Res.* 23:1417-1450; Torchilin (2005) *Nat. Rev. Drug Discov.* 4:145-160).

Nanohybrid particles composed of a nanoparticle surrounded by a multifunctional ligand or targeting moiety have been suggested (WO 2006/095936; US 2010/0266491). Moreover, drug delivery vectors containing stealth agents are described in WO 2009/039502. Although hybrid systems that incorporate PEI into liposomes or biodegradable nanoparticles have been suggested (Ko, et al. (2009) *J. Control. Release* 133:230-237; Kim, et al. (2005) *Int. J. Pharm.* 298: 255-262; Son & Kim (2010) *Biomaterials* 31:134-143), the kinetics and interactions with cells have not been analyzed.

SUMMARY OF THE INVENTION

The present invention is a nanohybrid drug delivery composition composed of a multivalent polymeric scaffold with a therapeutic agent and targeting agent attached thereto; and a shell encapsulating the polymeric scaffold. In one embodiment, the shell is a liposome composed of a phospholipid selected from the group of egg phosphatidylcholine, egg phosphatidylethanolamine, soy bean phosphatidylcholine, lecithin, sphingomyelin, synthetic phosphatidylcholine, lyso-phosphatidylcholine, phosphatidylglycerol, phosphatidic acid, phosphatidylethanolamine, and phosphatidylserine, wherein the phospholipid can be modified with a long-circulating agent or cryoprotectant. In another embodiment, the shell is polymeric nanoparticle composed of a polymer selected from the group of poly-(γ-L-glutamyl-glutamine), poly-(γ-L-aspartylglutamine), poly-L-lactic acid, poly-(lactic acid-co-glycolic acid), polyalkylcyanoacrylate, polyanhydrides, polyhydroxyacids, polypropylfumerate, polyamide, polyacetal, polyether, polyester, poly (orthoester), polycyanoacrylate, [N-(2-hydroxypropyl) methacrylamide] copolymer, polyvinyl alcohol, polyurethane, polyphosphazene, polyacrylate, polyurea, polyamine polyepsilon-caprolactone, and copolymers thereof, wherein the polymer is modified or derivatized to enhance proteolytic resistance, improve circulating half-life, reduce antigenicity, reduce immunogenicity, reduce toxicity, improve solubility, or improve thermal or mechanical stability. In particular embodiments, the shell is biodegradable. In certain embodiments the multivalent polymeric scaffold is cationic and is composed of a polyamide, a polysaccharide, a polyanhydride, poly-L-lysine, a polyacrylamide, a polymethacrylate, a polypeptide, a polyethylene oxide, a polyethyleneimine, poly(amidoamine) (PAMAM) or PAMAM(ethylenediamine-EDA). Therapeutic agents attached to the scaffold include anti-cancer agents, anti-angiogenic agents, or anti-viral agents, which can be targeted to a cancer cell or immune cell. In yet other embodiments, the scaffold or shell, or both scaffold and shell have an imaging attached thereto. A pharmaceutical composition and kit containing the nanohybrid drug delivery composition are provided, as is a method for preventing or treating a disease or condition using the instant nanohybrid drug delivery composition.

DETAILED DESCRIPTION OF THE INVENTION

Figure 1:
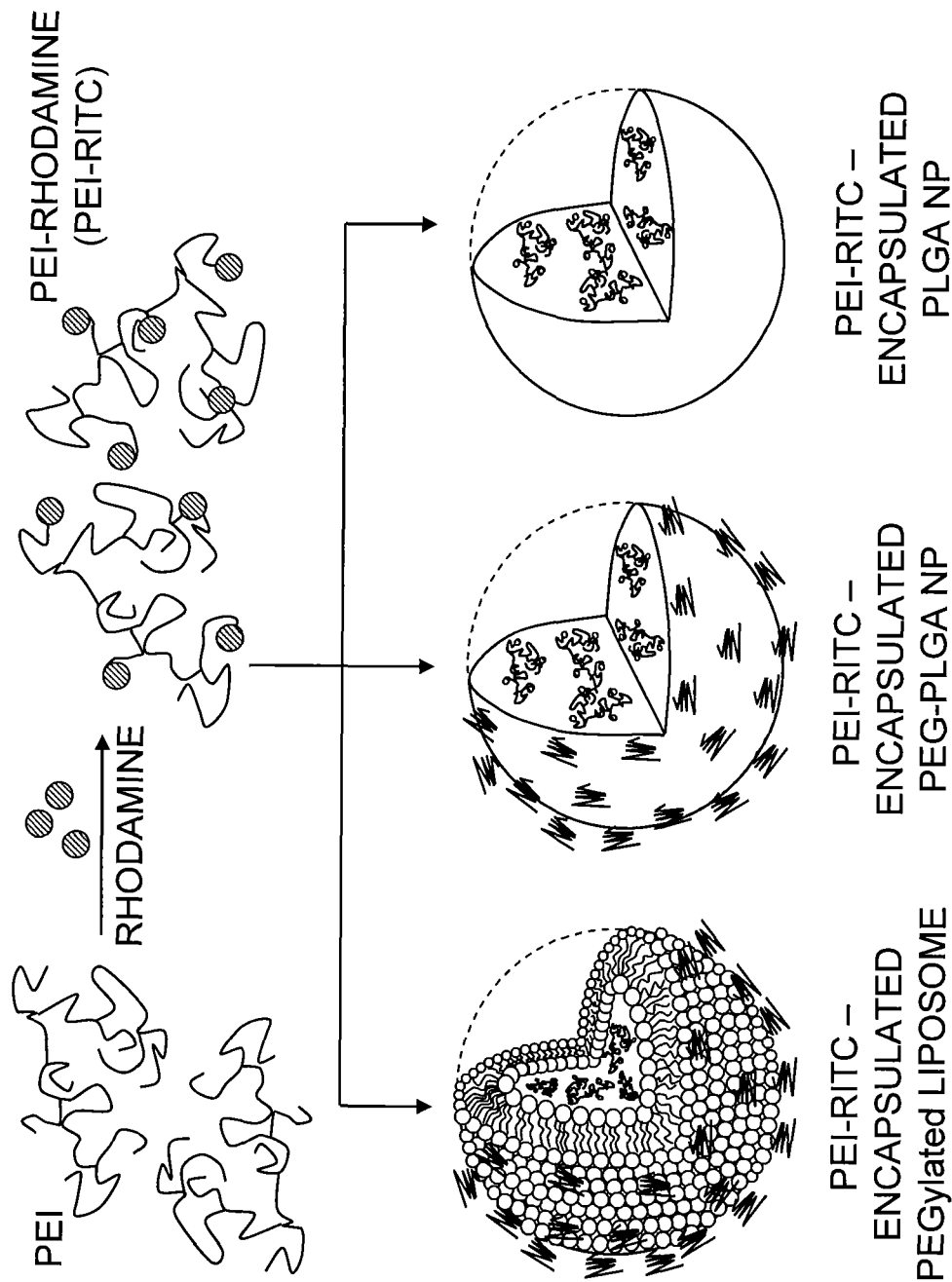
FIG. 1 is a schematic diagram of preparation of the three nanohybrid systems used in this study; PEI-RITC (PEI conjugated to rhodamine) encapsulated in a PEGylated liposome, PEI-RITC encapsulated in a polyethylene glycol-b-polylactide-co-glycolide (PEG-PLGA) nanoparticle (NP), and PEI-RITC encapsulated in a PLGA nanoparticle.

Although bioactive polymers such as cationic polymers have demonstrated potential as drug carriers and nonviral gene delivery vectors, high toxicity and uncontrolled, instantaneous cellular interactions of those vectors have hindered the successful implementation in vivo. Fine control over the cellular interactions of a potential drug/gene delivery vector is thus needed. A nanohybrid composition has now been designed that combines multivalent polymers with protective outer layers composed of polymeric nanoparticles (NPs) or liposomes. By way of illustration, commonly used polycation polyethylenimine (PEI) was employed after conjugation with rhodamine (RITC). The PEI-RITC conjugates were then encapsulated into: i) polymeric nanoparticles composed of either polylactide-co-glycolide (PLGA) or polyethylene glycol-b-polylactide-co-glycolide (PEG-PLGA); or ii) PEGylated liposomes, resulting in nanohybrid compositions. By comparing the release profiles, cytotoxicity, and cellular uptake of these PEI-based nanohybrids, it was demonstrated that fine control over release and cellular uptake kinetics of the nanohybrids could be achieved depending on the type of the outer layers. For example, in a cytotoxicity assay using MCF-7 cells, it was shown that liposome-based nanohybrids exhibited the least toxicity, followed by PEG-PLGA- and PLGA-based nanoparticles after a 24-hour incubation. A difference in kinetics of cellular uptake was also observed; the liposome-based compositions being the fastest and PLGA-based compositions being the slowest. These results indicate that enhanced targeting efficacy is possible through sequential utilization of passive and active targeting. The passive targeting utilizes the enhanced permeation and retention (EPR) effect that is characteristic of tumor biology. The active targeting typically involves specific ligand-receptor interactions by which drugs are directed to receptors that are uniquely overexpressed by target cells.

Accordingly, the present invention is a nanohybrid drug delivery composition, i.e., a particle in which a nanocore is surrounded or encapsulated in a matrix or shell. In other words, a smaller particle within a larger particle. In certain preferred embodiments, the nanohybrid composition is a nanocore inside a liposome. In other embodiments, the nanocore is surrounded by a polymeric matrix or shell (e.g., a polymeric nanoparticle). To exploit the enhanced permeation and retention (EPR effect, the instant nanohybrid drug delivery composition has, in some embodiments, a diameter in the range of 50 to 200 nm. In other embodiment, the instant nanohybrid drug delivery composition has a diameter in the range of 100 to 150 nm.

The nanocore of the instant nanohybrid drug delivery composition is a multivalent polymeric scaffold with a therapeutic agent and targeting agent attached thereto. A scaffold of the invention is multivalent in the sense that the polymeric scaffold or backbone has multiple reactive functional groups, such as amine, carboxylic acids, anhydride, or succinimide groups. In this respect, multiple therapeutic agents and/or multiple targeting agents containing any of a number of different reactive functional groups, such as amine, carboxylic acids, anhydride, or succinimide groups, can be reacted with appropriate groups on the polymeric scaffold. Alternately, monomeric units that could be joined to one another to form a polymeric backbone or scaffold are first reacted with the therapeutic agents and/or multiple targeting agents and the resulting monomers are polymerized.

For active cellular targeting, the nanocores of the instant compositions are preferably in the range from 1 nm to 50 nm in their greatest diameter. More preferably, the nanocores range from 1 to 40 nm in their greatest diameter, most preferably from 3 to 20 nm in their greatest diameter. The nanocores may be analyzed by dynamic light scattering and/or scanning electron microscopy to determine the size of the particles. A nanocore can have any shape and any morphology. Examples of nanocores include nanopowders, nanoclusters, nanocrystals, nanospheres, nanofibers, and nanotubes. Given its nanoscale size, the nanocore scaffold of the invention is readily excreted. Therefore, the nanocore scaffold employed need not be biodegradable, but in particular embodiments, the nanocore scaffold is biocompatible, i.e., not toxic to cells. Scaffolds are "biocompatible" if their addition to cells in vitro results in less than or equal to 30%, 20%, 10%, 5%, or 1% cell death and do not induce inflammation or other such unwanted adverse effects in vivo.

Suitable multivalent polymeric scaffolds are known to those skilled in the art, and can be selected depending on the agents with which it is operatively associated as well as the desired properties of the scaffold. In some embodiments, the multivalent polymeric scaffold is a linear molecule with multiple branches. In other embodiments, the multivalent polymeric scaffold is a dendritic molecule. In certain embodiments, the multivalent polymeric scaffold is a dendrimer or dendron.

Any of a variety of polymeric scaffolds or backbones can be used in the nanocore of the instant composition. For example, the polymeric scaffold may include, but is not limited to, a polyamide, a polysaccharide, a polyanhydride, poly-L-lysine, a polyacrylamide, a polymethacrylate, a polypeptide, a polyethylene oxide, a polyethyleneimine (PEI), or a dendrimer such as poly(amidoamine) (PAMAM) and PAMAM(ethylenediamine-EDA) dendrimers or modified versions thereof, e.g., hydroxylated, acetylated, or carboxylated versions of said polymers. Other suitable polymeric backbones are described, e.g., in WO98/46270 (PCT/US98/07171) or WO98/47002 (PCT/US98/06963). The multivalent polymeric scaffold molecules can have a configuration selected from linear, branched, forked or star-like.

In some embodiments, at least a portion of the multivalent polymeric scaffold molecule may be hydrophobic. In some embodiments, at least a portion of the multivalent polymeric scaffold molecule may be hydrophilic. In another embodiment, a portion of the multivalent polymeric scaffold molecule may be hydrophobic, and a different portion of the molecule may be hydrophilic. In particular embodiments, the multivalent polymeric scaffold molecule is cationic. In other embodiments, the multivalent polymeric scaffold molecule is electronically neutral. In still other embodiments, the multivalent polymeric scaffold molecule is anionic. Those skilled in the art will recognize that various starting materials may be selected to obtain a multivalent polymeric scaffold molecule that exhibits the desired properties.

According to the present invention, a therapeutic agent and targeting agent are attached to or operatively associated with the multivalent polymeric scaffold of the nanocore. In this context, "attached" or "operatively associated" refers to an electronic interaction between the scaffold and the agents. Such interaction may take the form of a chemical bond, including, but not limited to, a covalent bond, a polar covalent bond, an ionic bond, an electrostatic association, a coordinate covalent bond, an aromatic bond, a hydrogen bond, a dipole, or a van der Waals interaction. Those of ordinary skill in the art understand that the relative strengths of such interactions may vary widely.

A "therapeutic agent" is a compound that, upon administration to a mammal in a therapeutically effective amount, provides a therapeutic benefit to the mammal. A therapeutic agent may be referred to herein as a drug. Those skilled in the art will appreciate that the term "therapeutic agent" is not limited to drugs that have received regulatory approval.

Therapeutic agents delivered by the compositions and methods of the present invention include small organic molecules, RNA, DNA, proteins, chemicals or peptides to block transcription, translation, intracellular signaling cascades, enzymes (kinases), proteosome activity, lipid metabolism, cell cycle, and membrane trafficking. Therapeutic agents delivered by the instant compositions and methods include agents that target proinflammatory mediators such as cytokine and chemokine genes, enzymes involved in generation of inflammatory mediators, receptors for cytokines, chemokines, lipid mediators, apoptosis, cytoplasmic signaling molecules involved in inflammatory cascades, e.g., NF-κB, STAT, Talin, Rap-1; tissue injury such as apoptosis, e.g., caspase, bcl-2; molecules important for cell activation and proliferation, e.g., cyclins, kinesin Eg5; molecules important for cell movement/migration/invasion, e.g., small G-proteins, cytoskeletal proteins; and oncogenes. Specific targeting of CD4 may also be used for blocking HIV infection. Moreover, specific targeting of Ku70 may be used for killing or suppressing cancer cells and specific targeting of Cyclin-D1 may be used for blocking proliferation.

In addition, compositions containing therapeutic agents for treating diseases such as viral diseases are also included in the present invention. One example of such a delivery agent is an siRNA which serves as a microbicides. This is useful for treatment and/or prevention of HSV, HPB and HIV. Such therapeutic agents are described in PCT/US2006/021758 and PCT/US2003/034424. Antiviral therapeutics also include viral entry inhibitors, viral assembly inhibitors, viral DNA and RNA polymerase inhibitors, viral reverse transcriptase inhibitors, viral protease inhibitors, viral integrase inhibitors, and inhibitors of viral shedding.

In particular embodiments, the therapeutic agent delivered by the compositions and methods of the present invention include chemotherapy agents. Such agents include, e.g., anticancer drugs such as paclitaxel, methotrexate, doxorubicin, cisplatin, tamoxifen and its metabolites (e.g., 4-hydroxytamoxifen and endoxifen); and anti-angiogenesis agents such as canstatin, proliferin-related proteins, restin, maspin, osteopontin, Secreted Protein Acidic and Rich in Cysteine (SPARC) protein, Vascular Endothelial cell Growth Inhibitor (VEGI), prolactin, prothrombin, Interferon (IFN)-alpha, IFN-beta, IFN-gamma, C-X-C motif chemokine 10 (CXCL10), Interleukin (IL)-4, IL-12, Metalloprotease and Thrombospondin domains protein (METH)-1 and METH-2, Tissue Inhibitors of Metalloproteinase (TIMP), cell division autoantigen 1 (CDA1), platelet factor-4, vasostatin, calreticulin, endostatin, angiostatin, thrombospondin (TSP)-1 and TSP-2, Angiopoietin 2, Vascular Endothelial Growth Factor Receptor (VEGFR)-1, and Novel SH2-containing Protein 1 (NSP-1). Other chemotherapeutic agents include, but are not limited to, a Transforming Growth Factor Beta (TGFβ) inhibitor, a gamma-type Peroxisome Proliferator-Activated Receptor (PPARγ) ligand, an angiotensin activity inhibitor, a Platelet-Derived Growth Factor (PDGF) inhibitor, a sodium channel inhibitor, and an apoptosis inducer.

The amount of therapeutic agent present in the therapeutic composition can vary over a wide range. The therapeutic agent can be about 25% to about 75% (weight/weight) of the total mass of the nanocore (wherein the mass of the therapeutic agent is included in the total mass of the nanocore). In other embodiments, the therapeutic agent can be about 30% to about 60% w/w of the total mass of the nanocore (same basis). In still other embodiments, the therapeutic agent can be about 40% to about 70% w/w of the total mass of the nanocore (same basis).

The term "targeting agent" refers to a compound that exhibits selectivity for a particular target organ, tissue or cell. A targeting agent is capable of directing a composition, with which it is operatively associated, to a particular target organ, tissue, or cell. As with the therapeutic agent, various targeting agents may be used in the composition and methods herein. In some embodiments, the targeting agent targets a cancer cell. One example of a targeting agent is the vitamin folic acid (FA), which binds folate receptors that are overexpressed in ~90% of human ovarian carcinomas. Luteinizing hormone-releasing hormone (LHRH) is another suitable targeting agent. LHRH is relatively small molecule (MW 1,182 Da), with the receptors overexpressed by breast, ovarian, and prostate cancer cells. As another example, the targeting agent is a retinoid such as retinol, retinal, retinoic acid, rexinoid, or derivatives or analogs thereof. Further examples of targeting agents include, but are not limited to, transferrin, RGD peptide, Herceptin, prostate-specific membrane antigen (PSMA)-targeting aptamers, and the like. In other embodiments, the targeting agent targets an immune cell. For targeting immune cells, the targeting agent can be a ligand of e.g., a T cell surface receptor.

Lectins can also be used to target mucin and the mucosal cell layer. Lectins of use in the invention include those isolated from *Abrus precatroius, Agaricus bisporus, Glycine max, Lysopersicon esculentum, Mycoplasma gallisepticum*, and *Naja mocambique*, as well as lectins such as Concanavalin A and Succinyl-Concanavalin A.

In particular embodiments, the targeting agent increases the selective delivery of the nanocore to a particular target organ, tissue or cell. Target organs may include, for example, the liver, pancreas, kidney, lung, esophagus, larynx, bone marrow, and brain. In some embodiments, the increase in selective delivery may be at least about two-fold as compared to that of an otherwise comparable composition lacking the targeting agent. In other embodiments, the therapeutic compositions described herein can increase the delivery of the nanocore containing a therapeutic agent to the target organ, tissue or cell by at least 10% as compared to that of an otherwise comparable composition lacking the target agent. In other embodiments, the therapeutic compositions described herein can increase the delivery of the nanocore to the target organ, tissue or cell by at least 25% or more as compared to that of an otherwise comparable composition lacking the target agent.

The amount of targeting agent present in the therapeutic composition can vary over a wide range. In some embodiments, the targeting agent can be about 1% to about 50% (weight/weight) of the total mass of the nanocore (wherein the mass of the targeting agent is included in the total mass of the nanocore). In other embodiments, the targeting agent may be about 10% to about 30% w/w of the total mass of the nanocore (same basis). In still other embodiments, the targeting agent may be about 20% to about 40% w/w of the total mass of the nanocore (same basis).

The compositions disclosed herein may be prepared in various ways. In some embodiments, one or more of the agents may be operatively associated with the multivalent polymeric scaffold through a covalent bond. When operatively associated through a covalent bond, one or more of the agents may be directly bonded to the multivalent polymeric scaffold. A variety of mechanisms known to those skilled in the art can be used to form the covalent bond between the one or more agents and multivalent polymeric scaffold, e.g., a condensation reaction. Additional methods for directly bonding one or more agents to a multivalent polymeric scaffold are known to those skilled in the art, and may be identified by routine experimentation informed by the guidance provided herein. For example, the one or more therapeutic agents and/or one or more multiple targeting agents can contain any of a number of different reactive functional groups for attachment or bonding to the functional groups on the polymeric scaffold. As is known to the skilled artisan, crosslinking chemistries include, but are not limited to, thioether, thioester, malimide and thiol, amine-carboxyl, amine-amine, and others listed in organic chemistry manuals, such as, Elements of Organic Chemistry, Isaak and Henry Zimmerman Macmillan Publishing Co., Inc., New York, N.Y. The instant agents can also be attached to the polymeric scaffold using a crosslinking reagent (e.g., glutaraldehyde (GAD), bifunctional oxirane (OXR), ethylene glycol diglycidyl ether (EGDE), N-hydroxysuccinimide (NHS), and a water soluble carbodiimide, such as 1-ethyl-3-(3-dimethylaminopropyl)carbodiimide (EDC)). The compositions herein can further have at least one hydrolysable linker between the therapeutic agent and scaffold and/or targeting agent and scaffold.

Targeting efficacy of the instant nanohybrid composition is enhanced by harnessing both mechanisms of passive and active targeting that complement each other. To achieve sequential passive and active targeting, not only does the instant composition contain an actively targeted polymeric scaffold nanocore, but it also includes the encapsulation of the nanocore within a shell. The terms "encapsulation," "encapsulating" and "entrapped," as used interchangeably herein, refer to the incorporation of a polymeric scaffold nanocore in a shell. Desirably, the shell facilitates the transport of the nanocore from one part of the body to a target cell or tissue and/or into a target cell or tissue. The carrier can be electronically charged (e.g., negatively-charged or positively-charged) or electronically neutral. In one embodiment, the polymeric scaffold nanocore is encapsulated in the interior of a liposome. In another embodiment, the polymeric scaffold nanocore is encapsulated in the interior of a polymeric nanoparticle.

A "liposome" refers to a lipid bilayer structure that contains lipids attached to polar, hydrophilic groups, forming a substantially closed structure in aqueous media that encapsulates a nanocore. A liposome may be composed of a single lipid bilayer (i.e., unilamellar) or it may composed of two or more concentric lipid bilayers (i.e., multilamellar). A liposome can be approximately spherical or ellipsoidal in shape.

Liposomes of the invention can be composed of a natural phospholipid, such as egg phosphatidylcholine, egg phosphatidylethanolamine, soy bean phosphatidylcholine, lecithin, and sphingomyelin. Alternatively, the liposome can include a synthetic phospholipid. Synthetic phospholipids include, but are not limited to, synthetic phosphatidylcholine, lyso-phosphatidylcholine, phosphatidylglycerol, phosphatidic acid, phosphatidylethanolamine, phosphatidylserine, and derivatives thereof.

In some embodiments, the outer surface of the liposome is modified. One example of such a modification is modification of the outer surface of the liposome with a long-circulating agent e.g., a hydrophilic polymer or glycosaminoglycans, to prevent the uptake of the liposomes into the cellular endothelial systems and enhance the uptake of the liposomes into the tissue of interest. Suitable hydrophilic polymers include polyethylene glycol, polymethylethylene glycol, polyhydroxypropylene glycol, polypropylene glycol, polymethylpropylene glycol and polyhydroxypropylene oxide. Examples of suitable glycosaminoglycans for use include, e.g., hyaluronic acid. The liposomes may also or alternatively be modified with a cryoprotectant, e.g., a sugar, such as trehalose, sucrose, mannose, glucose or HA. The term "cryoprotectant" refers to an agent that protects a lipid particle subjected to dehydration-rehydration, freeze-thawing, or lyophilization-rehydration from vesicle fusion and/or leakage of vesicle contents. Methods and specific examples for coating a liposome are provided in PCT/US2007/010075.

A nanoparticle is a nanoparticle which is prepared from polymers and has at least one dimension of less than ~200 nm. Various polymeric nanoparticles can be used in the compositions disclosed herein. Suitable polymers are known to those skilled in the art. In some embodiments, the polymer is a non-cationic polymer. In accordance with this embodiment, the non-cationic polymer is anionic (i.e., negatively-charged). In other embodiments, the non-cationic polymer is electronically neutral. In yet other embodiments, the polymer is water-soluble. In still other embodiments, the polymer is biodegradable. Polymers of use in the instant nanoparticle can be homopolymeric or be composed of a mixture of polymers or a copolymer. Examples of polymers of the instant nanoparticle shell include, but are not limited to, poly-(γ-L-glutamylglutamine) (PGGA), poly-(γ-L-aspartylglutamine) (PGAA), poly-L-lactic acid (PLLA), poly-(lactic acid-co-glycolic acid) (PLGA), polyalkylcyanoacrylate (PACA), polyanhydrides, polyhydroxyacids, polypropylfumerate, polyamide, polyacetal, polyether, polyester, poly(orthoester), polycyanoacrylate, [N-(2-hydroxypropyl)methacrylamide] (HPMA) copolymer, polyvinyl alcohol, polyurethane, polyphosphazene, polyacrylate, polyurea, polyamine polyepsilon-caprolactone (PCL), and copolymers thereof.

The radius and aggregation numbers of the resulting polymeric nanoparticles is highly dependent on the length of the constituent blocks. The dependence of the radius and aggregation number on the hydrophobic and hydrophilic block lengths. Therefore, the polymer selected will control size (measured by dynamic light scattering) and biodegradability (measured by a fluorimeter that detects the released fluorescence-labeled nanovectors) of the nanoparticles.

To improve the characteristics of the instant nanoparticles, the polymer of the nanoparticle can be modified or derivatized. For example, conjugation of polymers to PEG and PEG-derivatives has been shown to enhance proteolytic resistance; markedly improve circulating half-life; reduce antigenicity, immunogenicity and toxicity; and improve solubility, thermal and mechanical stability (Chapman (2002) *Adv. Drug Del. Rev.* 54:531-545; Harris, Ed., Poly(Ethylene Glycol) Chemistry: Biotechnical and Biomedical Applications, Plenum Press, NY, 1991). Moreover, different end groups of PEG, such as hydroxyl, carboxylate, and methoxy groups can vary the blood circulation time of the nanoparticles.

In yet another embodiment of the invention, the composition of the invention further includes one or more imaging agents. In some embodiments, the nanocore has an imaging agent attached to the multivalent scaffold. In other embodiments, the shell has an imaging agent attached thereto. In further embodiments, the multivalent scaffold and shell each include an imaging agent, wherein said imaging agent can be the same or different for the multivalent scaffold and shell. In this respect, the instant composition can deliver single or dual imaging agents. Many appropriate imaging agents are known in the art (see, e.g., U.S. Pat. Nos. 5,021,236 and 4,472,509, both incorporated herein by reference). Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, carbon$^{14}$, chromium$^{51}$, chlorine$^{36}$, cobalt$^{57}$, cobalt$^{58}$, copper$^{62}$, copper$^{64}$, copper$^{67}$, fluorine$^{18}$, gallium$^{67}$, gallium$^{68}$, hydrogen$^{3}$, iodine$^{123}$, iodine$^{124}$, iodine$^{125}$, iodine$^{131}$, indium$^{111}$, iron$^{52}$, iron$^{59}$, lutetium$^{177}$, phosphorus$^{32}$, phosphorus$^{33}$, rhenium$^{186}$, rhenium$^{188}$, and selenium$^{75}$. I$^{125}$ is often being preferred for use in certain embodiments, and indium$^{111}$ is also often preferred due to its low energy and suitability for long-range detection.

In certain embodiments, the imaging agent is a secondary binding ligand or an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference. These fluorescent labels are preferred for in vitro uses, but may also be of utility in in vivo applications, particularly endoscopic or intravascular detection procedures.

In alternative embodiments, the imaging agent is a fluorescent marker. Non-limiting examples of photodetectable labels include ALEXA 350, ALEXA 430, AMCA, aminoacridine, BODIPY 630/650, BODIPY 650/665, BODIPY-FL, BODIPY-R6G, BODIPY-TMR, BODIPY-TR, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, Edans and TEXAS RED. These and other luminescent labels may be obtained from commercial sources such as Molecular Probes (Eugene, Oreg.), and EMD Biosciences (San Diego, Calif.).

Chemiluminescent agents of use may include luminol, isoluminol, an aromatic acridinium ester, an imidazole, an acridinium salt and an oxalate ester, or a bioluminescent compound such as luciferin, luciferase and aequorin. Diagnostic conjugates may be used, for example, in intraoperative, endoscopic, or intravascular tumor or disease diagnosis.

It is contemplated that, as with the other modifications or derivatizations disclosed herein, imaging agents can be attached to the multivalent scaffold and/or shell by known methods and functional groups.

Encapsulation of the polymeric scaffold and controlled selection of the size of the resulting nanohybrid drug delivery composition can be carried out as exemplified herein or using any other suitable method or combination of methods depending on the material of the shell. Such method can include, e.g., conventional double emulsion or film hydration methods. In particular embodiments, compositions composed of polymeric nanoparticles are prepared by a Flash NanoPrecipitation (FNP) method, which employs rapid micromixing to create high supersaturation and rapid nucleation and growth of the drug or desired compound. Using this method, block copolymers can kinetically arrest aggregation by self-assembly to produce a tunable and narrow particle size distribution. Using high-energy micromixers, mixing occurs on the order of milliseconds, thereby enabling the process to be run under "homogeneous" conditions such that the effect of mixing is not convoluted with the precipitation process. Precise control of particle size over the range from 50 nm to 500 nm occurs by balancing the induction time of the block copolymer ($\tau_{sa}$) and the nucleation and growth time of the solute ($\tau_{ng}$). Since the process relies on kinetic and not solely on thermodynamic control of self-assembly of hydrophobic solutes and block copolymers, the loading rate of the active compound can be up to 90 wt %. It should be noted that this process enables the co-assembly of hydrophobic organic solutes as well as of organic and inorganic nano-particulate materials and preformed colloids. Nanoparticle size can be macroscopically controlled by the mixing process, supersaturation rate, and drug loading rate. The supersaturation rate is defined as the equilibrium solubility of the solute in the final mixed solvent stream divided by the initial concentration before mixing.

Using this method, it was successfully demonstrated that nanoparticles can be fabricated with a very narrow size distribution using small organic compounds, such as SR13668, paclitaxel (TAXOL), estradiol, rifampicin, vitamin E, and β-carotene, with amphiphilic diblock copolymers, such as poly(ethylene glycol)-bpoly(caprolactone) (PEG-b-PCL), poly(ethylene glycol)-b-poly(lactic acid) (PEG-b-PLA), poly (acrylic acid)-b-poly(butyl acrylate) (PAA-b-PBA), and poly (ethylene glycol)-b-polystyrene (PEG-b-PS). More specifically, β-carotene was encapsulated in PEG-b-PS (MW 3,000-b-1,000) particle sizes using various supersaturation rates and mixing processes characterized by the Reynolds number. A 1:1 (wt:wt) ratio of polymer to β-carotene was significantly higher than the loading reported for partitioning of solutes into polymeric micelles. Resulting particle sizes were determined by the drug concentrations and the volumetric ratio of the incoming streams. By increasing the supersaturation rate, the diameter of β-carotene-containing polymeric nanoparticles decreased from 250 nm to 70 nm. Nanoparticle size was independent of the mixing process when the mixing was fast enough. In separate experiments, the ratio of polymer to active compound was varied between 3:1 and 1:10 (wt:wt), loadings that have not been achieved by any other process for producing narrow size distribution nanoparticles.

The present invention in various embodiments provides pharmaceutical compositions containing a therapeutically effective amount of the instant nanohybrid drug delivery composition in admixture with a pharmaceutically acceptable carrier or excipient. Such carriers include, but are not limited to, saline, buffered saline, dextrose, water, glycerol, ethanol, and combinations thereof. The formulation should suit the mode of administration and therefore, the formulation can be prepared with or without an agent or device for sustained release, for delivery locally or systemically. An "effective amount" as the term is used herein is an amount of a therapeutic agent or combination of agents sufficient to achieve a recognized medical endpoint, e.g., a decrease in tumor size or proliferation or a decrease in the symptoms of a viral infection. The effective amount can be determined empirically by a skilled artisan according to established methods of measurement of relevant parameters, as described herein.

The compositions herein can further include wetting or emulsifying agents, or pH buffering agents. The composition can be a liquid solution, suspension, emulsion, tablet, pill, capsule, sustained release formulation, or powder. The compositions can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In an exemplary embodiment, a composition herein is formulated in accordance with routine procedures as a pharmaceutical composition adapted, for example, for subcutaneous administration to human beings. Typically, compositions for subcutaneous administration are solutions in sterile isotonic aqueous buffer. Where necessary, the composition may also include a solubilizing agent and a local anesthetic to ameliorate pain at the site of the injection. Generally, the ingredients are provided either separately or mixed together in unit dosage form, for example, as a dry, lyophilized powder or water-free concentrate in a hermetically sealed container such as an ampoule or sachet, for example, indicating the quantity of active agent. Where the composition is to be administered by infusion, it can be dispensed with an infusion bottle containing sterile pharmaceutical grade water, buffer, or saline. Where the composition is administered by injection, an ampoule of sterile water or saline for injection can be provided so that the ingredients may be mixed prior to administration. The compositions herein can in various components thereof be formulated as suppositories, which contain active ingredient in the range of about 0.5% to about 10% by weight; oral formulations preferably contain about 10% to about 95% active ingredient by weight. A daily dose is administered as a single dose, or is divided into a plurality of smaller fractional doses, to be administered several times during the day.

As used herein, a dosing schedule refers to a protocol for administering any of the compositions as described herein, in an effective dose, administered simultaneously or within a particular interval of each other, for example, within one day of each other, or as a combined preparation, or separately, and includes the amount of the composition delivered per unit time such as per day, and the duration or period of time over which each composition is administered.

Aggressive tumors inherently develop leaky vasculature with 100 to 800 nm pores due to rapid formation of vessels that must serve the fast-growing tumor. This defect in vasculature coupled with poor lymphatic drainage serves to enhance the permeation and retention of drug delivery particles within the tumor region. This is often called the EPR effect. This phenomenon provides for "passive targeting." The basis for increased tumor specificity is the differential accumulation of drug-loaded particles in tumor tissue versus normal cells, which results from particle size rather than binding. Normal tissues contain capillaries with tight junctions that are less permeable to nanosized particles. Passive targeting can therefore result in increases in drug concentrations in solid tumors of several-fold relative to those obtained with free drugs.

Passive delivery may also be directed to lymphoid organs of the mammalian immune system, such as lymphatic vessels and spleen. These organs are finely structured and specialized in eliminating invaders that have gained entry to tissue fluids. Nanosized particles may easily penetrate into lymphatic vessels taking advantage of the thin walls and fenestrated architecture of lymphatic microvessels. Passive targeting to the spleen is via a process of filtration. Indeed the spleen filters the blood of foreign particles larger than 200 nm. This function facilitates splenic targeting with nanosized particles encapsulating drug for effective treatments against several hematological diseases.

Given that the instant composition has a controlled size range, which takes advantage of passive targeting, and also provides active targeting to reduce side effects and cytotoxicity of the polymeric scaffold, the present invention also provides methods for preventing or treating a disease or condition such as cancer (e.g., gastric, lung, breast, ovarian, liver, bronchogenic, nasopharyngeal, laryngeal, pancreatic, bladder, colon, and cervical cancers), viral infection or other diseases that induce leaky vasculature, e.g., inflammatory diseases, macular degeneration and diabetes. The method involves the step of administering to a subject in need thereof a composition as described herein in an amount sufficient to decrease one or more signs or symptoms of the disease or condition. Such symptoms can include, but are not limited to a decrease in cancer cell proliferation, a decrease in tumor size, a decrease in the number of infective viral units in the subject, or a decrease in vascular leakage as determined by routine methods. Administering the composition described herein reduces signs or symptoms of the disease or condition in a subject, compared to the signs or symptoms in subject prior to administering the composition, or compared to a subject not receiving such treatment.

Given the instant design, the non-specific interaction of the nanohybrid composition during circulation will be avoided until the biodegradable polymeric nanoparticles accumulate (due to the EPR effect) to the tumor sites or sites of vascular leakage. The polymer shell will degrade (e.g., facilitated by the low pH at tumor sites), and nanocore will be released and interact only with the cells of interest. One of the key attributes of the instant nanohybrid composition is that the nanocores will not interact with cells if the system accumulates in undesired healthy tissue as the cells in the proximity will have a low probability of expressing the same protein targets. The stealth effect of PEG outer-layers on the nanohybrid composition will increase the circulation time and prevent undesired active targeting to non-target cells until the composition reaches tumor sites in the body. In addition, the conjugated drugs to the scaffold will act as a pro-drug, minimizing the multidrug resistance (MDR) effect.

The amount of the therapeutic of the invention which will be effective in the treatment of a particular disease or condition will depend on the nature of the disease or condition, and can be determined by standard clinical techniques. The precise dose to be employed in the formulation will also depend on the route of administration, and the seriousness of the disease or condition, and should be decided according to the judgment of the practitioner and each patient's circumstances. Effective doses may be extrapolated from dose-response curves derived from in vitro or animals or animal model test systems, by one of ordinary skill in the art of pharmacology. Dosages of the compositions to be administered to a subject are adjusted for known variations from species to species using standard data encompassing criteria for absorption, distribution, half-life kinetics in circulation, metabolism, excretion, and toxicology of the compositions of the embodiments herein. Suitable dosage ranges for administration are generally about 0.01 micrograms to about 10,000 micrograms of each active compound per kilogram body weight per day, for example, about 0.01 micrograms to about 1 microgram/kg, about 0.1 micrograms/kg to about 10 micrograms/kg, about 1 microgram/kg to about 500 micrograms/kg, or about 10 micrograms/kg to about 10 mg/kg of body weight per day. Suitable dosage ranges for administration are thus generally about 0.01 micrograms/kg body weight/day to about 10 mg/kg body weight/day.

The invention in other embodiments provides a pharmaceutical pack or kit comprising one or more containers filled with one or more of the ingredients of the pharmaceutical compositions of the invention. In such a pack, or kit can be found a container having a unit dosage of the nanohybrid drug delivery composition. Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration. As a preferred dosage for administration is intravenous, the unit dosage can be prepackaged in an infusion bottle or bag.

The following non-limiting examples are provided to further illustrate the present invention.

Example 1

Materials and Methods

Materials. Branched PEI ($M_n$ 10,000), PLGA (50:50, $M_w$ 40,000-75,000), poly(vinyl alcohol) (PVA, 87-89% hydrolyzed, $M_w$ 13,000-23,000), rhodamine B isothiocyanate (RITC, mixed isomers), dichloromethane (DCM), pyridine, p-nitrophenyl chloroformate (p-NPC), triethyleamine (TEA), diethyl ether, and cholesterol were all obtained from Sigma-Aldrich (St. Louis, Mo.). Amine-terminated methoxy PEG (mPEG-NH$_2$) ($M_w$ 5,000) was obtained from Nektar (Huntsville, Ala.). 1,2-distearoyl-sn-glycero-3-phosphoethanolamine-N-mPEG-2000 (DSPE-PEG 2000), 1,2-distearoyl-sn-glycero-3-phosphocholine (DSPC), and 1,2-dioleoyl-sn-glycero-3-phospho-(1'-rac-glycerol) sodium salt (DOPG) were purchased from Avanti Polar Lipids Inc. (Alabaster, Ala.). All other chemicals used in this study were purchased from Sigma-Aldrich unless specified otherwise.

Preparation and Characterization of PEI-RITC Conjugates. PEI was fluorescently labeled by conjugation with RITC using a similar method described in the art (Hong, et al. (2004) supra). RITC (5.4 mg, $1.0 \times 10^{-5}$ mol), dissolved in 1 mL deionized distilled water (ddH$_2$O), was added to PEI (20.0 mg, $2.0 \times 10^{-6}$ mol) dissolved in 4 mL ddH$_2$O. The pH of the mixture was adjusted to 9.0 using 1.0 N hydrochloric acid (HCl), followed by vigorous mixing at room temperature (RT) for 24 hours. Unreacted RITC was removed using membrane dialysis (SPECTRA/POR dialysis membrane, MWCO 3,500, Spectrum Laboratories Inc., Rancho Dominguez, Calif.) in 3 L of phosphate-buffered saline (PBS) for 2 days, changing the buffer every 12 hours, followed by dialysis in ddH$_2$O for 2 days, changing the water every 12 hours. The purified PEI-RITC conjugates were lyophilized over 2 days using a LABCONCO FREEZONE 4.5 system (Kansas City, Mo.) and stored at $-20°$ C.

UV/Vis Spectroscopy. A series of RITC solutions in ddH$_2$O (6.3, 12.5, 25.0, 37.5, and 50.0 µg/mL) were prepared and used as standards to calculate the RITC content of the conjugates in subsequent measurements. PEI-RITC conjugates were dissolved in ddH$_2$O at a concentration of 100 µg/mL. UV spectra were recorded against ddH$_2$O using a DU800 UV/Vis Spectrophotometer (Beckman Coulter, Calif.). A standard curve of RITC absorbance versus concentration was constructed, and the concentration of RITC in the PEI-RITC solution was calculated based on Beer's Law. The number of RITC molecules per PEI chain was determined based on the amount of RITC in the PEI-RITC solution.

Synthesis and Characterization of PEG-PLGA Copolymer. PEG-PLGA block copolymer used in this study was synthesized from mPEG-NH$_2$ and PLGA using a similar method described in the art (Yoo & Park (2001) *J. Control. Release* 70:63-70). Five hundred milligrams of PLGA ($1.3 \times 10^{-5}$ mol) were dissolved in 8 mL of DCM, to which 5.1 µL ($6.3 \times 10^{-5}$ mol) of pyridine were added. p-NPC (12.6 mg, $6.3 \times 10^{-5}$ mol) was dissolved in 1 mL of DCM, and then added drop-wise to the PLGA and pyridine solution under vigorous stirring, and the reaction was carried out at RT for 24 hours. The reaction product (p-NP-PLGA) was then precipitated using ice-cold diethyl ether and vacuum filtered. Next, p-NP-PLGA (400 mg, $1.0 \times 10^{-5}$ mol) was dissolved in 8 mL of DCM. mPEG-NH$_2$ (93.8 mg, $1.9 \times 10^{-5}$ mol) was dissolved in 3 mL of DCM, to which 7 µL ($5.0 \times 10^{-5}$ mol) of TEA were added. The mPEG-NH$_2$ and TEA solution was then added drop-wise to the p-NP-PLGA solution under vigorous stirring, and the reaction was carried out at RT for 24 hours. The final product (PEG-PLGA) was precipitated using ice-cold diethyl ether and vacuum-filtered. PEG-PLGA was characterized using $^1$H NMR in CDCl$_3$ using a 400 MHz Bruker DPX-400 spectrometer (Bruker BioSpin Corp., Billerica, Mass.).

Encapsulation of PEI-RITC Conjugates into Polymeric NPs. PLGA and PEG-PLGA NPs were prepared using a double emulsion method (Perez, et al. (2001) *J. Control. Release* 75:211-224). Briefly, 20 mg of either PLGA or PEG-PLGA were dissolved in 1 mL of DCM. PEI-RITC was dissolved in ddH$_2$O at a concentration of 1 mg/mL, and 100 µL of the solution were added to either PLGA or PEG-PLGA solution in DCM. The mixture was sonicated for 1 minute using a Misonix XL Ultrasonic Processor (100% duty cycle, 475 W, ⅛" tip, QSONICA, LLC, Newtown, Conn.). Two milliliters of 3% PVA solution in ddH$_2$O was then added to the mixture, followed by sonication for 1 minute at 100% duty cycle. The double emulsion was then poured into 20 mL of 0.3% PVA in ddH$_2$O, and vigorously stirred at RT for 24 hours to evaporate DCM. The resulting aqueous solution was transferred to NALGENE high-speed centrifuge tubes (Fisher Scientific, Pittsburg, Pa.). PVA and unencapsulated PEI-RITC were removed by ultracentrifugation at 20,000 rpm for 30 minutes using a BECKMAN AVANTI J25 Centrifuge (Beckman Coulter, Brea, Calif.). After washing the NPs five times with ddH$_2$O, the pellet was resuspended in ddH$_2$O, lyophilized over 2 days, and stored at $-20°$ C.

Characterization of the PEI-RITC-Encapsulated Polymeric NPs. Particle size (diameter, nm) and surface charge (zeta potential, mV) of the NP-based nanohybrids were obtained from three repeat measurements by quasi-elastic laser light scattering using a NICOMP 380 Zeta Potential/Particle Sizer (Particle Sizing Systems, Santa Barbara, Calif.). The nanohybrid particles were suspended in ddH$_2$O at a concentration of 100 µg/mL, filtered through a 0.45 µm syringe filter, and briefly vortexed prior to each measurement. Loading was defined as the PEI-RITC content of the NP-based nanohybrids. Five milligrams of NP-based nanohybrids were completely dissolved in 1 mL of 0.5 M NaOH, followed by filtration through a 0.45 µm syringe filter. The fluorescence intensity from the filtrates containing PEI-RITC was then measured using a SPECTRAMAX GEMINIXS microplate spectrofluorometer (Molecular Devices, Sunnyvale, Calif.). The amount of PEI-RITC released was determined from a standard curve of PEI-RITC fluorescence versus concentration in 0.5 M NaOH. Loading was expressed as µg PEI-RITC/mg PLGA or PEG-PLGA. Loading efficiency was defined as the ratio of the actual loading obtained to the theoretical loading (amount of PEI-RITC added divided by the mass of PLGA or PEG-PLGA used in each formulation).

Scanning Electron Microscopy (SEM). The surface morphology of PLGA and PEG-PLGA NPs was examined using a JEOL-JSM 6320F field emission microscope (JEOL USA, Peabody, Mass.). Freeze-dried NP samples were placed onto a carbon adhesive strip mounted on an aluminum stub. Samples were sputter-coated with Pt/Pd at a coating thickness of 6 nm (POLARON E5100 sputter coater system, Polaron, UK) and then visualized at an accelerating voltage of 5.0 mV and 8.0 mm working distance.

Encapsulation of PEI-RITC Conjugates into Liposomes. Unilamellar liposomes were prepared using a film hydration method followed by extrusion (Ko, et al. (2009) supra). Briefly, DOPG (5.0 mg, 6.3×10$^{-6}$ mol), DSPC (4.9 mg, 6.2×10$^{-6}$ mol), Cholesterol (2.4 mg, 6.2×10$^{-6}$ mol, and DSPE-PEG 2000 (1.8 mg, 6.3×10$^{-7}$ mol) were dissolved in 5 mL of DCM in a round-bottom flask. The flask was connected to a rotary evaporator (ROTAVAPOR RII, Buchi, Switzerland) at 50° C. for 1 hour to evaporate DCM until completely dried. The dried lipid film was hydrated in 1 mL of 0.1 mg/mL PEI-RITC solution in ddH$_2$O, followed by vortexing for 15 minutes to form multilamellar liposomes. Multilamellar liposomes were sonicated in a bath sonicator for 30 minutes, and then extruded 20 times through a polycarbonate membrane of 100 nm pore size using a LIPOFAST Pneumatic extruder (Avestin Inc., Ottawa, Canada). The resulting unilamellar liposome suspension was centrifuged at 20,000 rpm for 1 hour to remove residual PEI-RITC. The pellet was resuspended in 1 mL of 5% sucrose, lyophilized over 2 days, and stored at −20° C.

Characterization of the PEI-RITC-Encapsulated Liposomes. Particle size (diameter, nm) and surface charge (zeta potential, mV) were measured using the same method described for polymeric NPs. Loading was determined by dissolving 10 mg of lyophilized liposomes in 1 ml of 0.1% TRITON X-100, followed by filtration through a 0.45 µm syringe filter and measuring the fluorescence of the filtrate. The amount of PEI-RITC released was determined from a standard curve of PEI-RITC fluorescence versus concentration in 0.1% TRITON X-100. Loading was expressed as µg PEI-RITC/mg lipids. Loading efficiency was calculated from the ratio of the actual measured loading to the theoretical loading (amount of PEI-RITC added divided by the mass of lipids and sucrose used in the formulation).

Transmission Electron Microscopy (TEM). Size and shape of liposomal nanohybrids was examined using TEM. Liposomes were dissolved in ddH$_2$O at a concentration of 1 mg/mL. One drop of the solution was then placed on a 300-mesh copper grid and left to dry overnight, followed by negative staining with 2% phosphotungstic acid (PTA). TEM images were acquired using a JEOL JEM 1220 (JEOL USA) at an accelerating voltage of 80 kV.

Release Kinetics Study of PEI-RITC-Encapsulated Nanohybrids. Five milligrams of each nanohybrid in microcentrifuge tubes were dispersed in 1 mL PBS (pH 7.4) or acetate buffer (pH 4.0) in triplicates, and the solutions were placed in a shaking water bath (37° C., 100 rpm). At designated time points (30 minutes, 1 hour, 2, 4, 6, 8, 10, 12 and 24 hours; every 2 days thereafter), solutions were centrifuged at 20,000 rpm for 5 minutes and the supernatants were collected. The nanohybrid systems were then redispersed in fresh PBS or acetate buffer and placed back in the water bath. The fluorescence of the supernatants was measured and the cumulative amount of PEI-RITC released over time was determined from a standard curve of PEI-RITC fluorescence versus concentration in either PBS or acetate buffer.

Cytotoxicity of PEI-RITC-Encapsulated Nanohybrids. MCF-7 cell line was obtained from ATCC (Manassas, Va.) and grown continuously as a monolayer in GIBCO Dulbecco's modified Eagle medium (DMEM, Invitrogen Corporation, Carlsbad, Calif.) in a humidified incubator at 37° C. and 5% CO$_2$. DMEM was supplemented with penicillin (100 units/mL), streptomycin (100 mg/mL), and 10% heat-inactivated fetal bovine serum (FBS) (Invitrogen Corporation, Carlsbad, Calif.) before use. For the assay, MCF-7 cells were seeded in 96-well plates at a density of 2×10$^4$ cells/well and grown in DMEM for 24 hours. Cells (n=4) were then treated with PEI-RITC or nanohybrid systems (PEI-RITC encapsulated liposomes, PEG-PLGA NPs, and PLGA NPs) at four PEI-RITC concentrations (1, 5, 10, and 30 µg/mL) for 1, 4, 24, and 48 hours. After each incubation time, cells were washed and incubated for an additional 24 hours in a normal culture condition. Cell viability was assessed using a CELL-TITER 96 AQUEOUS One Solution (MTS) Assay (Promega, Madison, Wis.) according to the manufacturer's protocol. The UV absorbance was measured at 490 nm using a LAB-SYSTEMS MULTISKAN Plus microplate reader (Labsystems, Finland). Mean cell viabilities were determined relative to a negative control (untreated cells). Statistical analysis was performed using ORIGINPRO 8.1 (OriginLab, Northampton, Mass.). Mean cell viabilities were compared using 1-way ANOVA followed by Tukey's post hoc test at $p<0.05$.

Cellular Uptake of PEI-RITC-Encapsulated Nanohybrids: Confocal Microscopy Observation. MCF-7 cells were seeded in 4-well chamber slides (MILLICELL EZ Slide, Millipore, Billerica, Mass.) at a density of 2.0×10$^5$ cells/well and incubated in DMEM for 24 hour. PEI-RITC (0.5 µg), liposomes (67 µg), PEG-PLGA NPs (242 µg), and PLGA NPs (106 µg) were each dispersed in 1 mL of DMEM to make the concentration of PEI-RITC constant at 0.5 µg/mL throughout all nanohybrids. Cells were treated with the three nanohybrids and unencapsulated PEI-RITC for 1, 4, 24, and 48 hours. Following the treatment, cells were washed with PBS three times, and then 50 µL of Wheat Germ Agglutinin ALEXA FLUOR® 488 conjugate (WGA-AF488, 5 µg/mL, Invitrogen Corporation, Carlsbad, Calif.) was added to each dish and incubated for 10 minutes at RT to stain the cell membrane. Cells were washed again with PBS, followed by fixation in 500 µL of 4% paraformaldehyde for 10 minutes at RT. After washing excess paraformaldehyde, cells were mounted with anti-photobleaching mounting media with DAPI (Vector Laboratory Inc., Burlingame, Calif.), and covered with glass cover slips. Cellular uptake was visualized using a ZEISS LSM 510 confocal laser scanning microscope (CLSM, Carl Zeiss, Germany). The 488 nm line of a 30 mW tunable argon laser was used for excitation of AF488, a 1 mW HeNe at 543 nm for RITC, and a 25 mW diode UV 405 nm laser for DAPI. Emission was filtered at 505-530 nm, 565-595 nm, and 420 nm for AF488, RITC, and DAPI, respectively.

Cellular Uptake of PEI-RITC-Encapsulated Nanohybrids: Flow Cytometry Measurements. MCF-7 cells were seeded in 12-well plates at a density of $1\times10^6$ cells/well and incubated in DMEM for 24 hours. Cells were then treated with unencapsulated PEI-RITC and the three nanohybrids under that same condition described in the cellular uptake experiment. After each incubation period, cells were washed with PBS and then suspended with trypsin/EDTA. Cell suspensions were centrifuged at 3500 rpm for 5 minutes, resuspended in 500 µL of 1% paraformaldehyde, and transferred to flow cytometry sample tubes. Fluorescence signal intensities from the samples were measured using a MOFLO cell sorter (BD, Franklin Lakes, N.J.) and data analysis was performed using Summit v4.3 software (Dako Colorado, Fort Collins, Colo.).

Example 2

Preparation and Characterization of PEI-RITC Conjugates and PEG-PLGA Copolymer

The UV/Vis measurements revealed the number of RITC molecules attached to a PEI chain. By constructing a calibration curve of UV absorbance of RITC against various concentrations at 555 nm ($\lambda_{max}$) the RITC concentration in a solution of the PEI-RITC conjugate was calculated from the absorbance at 555 nm. The molar ratio of PEI and RITC was then calculated by converting the concentration values to number of moles. The results indicated the presence of 6.2 RITC molecules per PEI chain. Particle size and zeta potential of the conjugates were measured to be 11.2 nm and 32.1 mV, respectively (Table 1). In addition, the chemical structure of PEG-PLGA was confirmed by $^1$H NMR. On the basis of the relative integration values of the characteristic peaks of each polymer, the ratio of the PEG block to the PLGA block was measured to be 1.3:1-2.4:1.

TABLE 1

| Formulation | Particle Size (nm) | Zeta Potential (mV) | Loading (µg/mg polymer or lipid) | Loading Efficiency (%) |
|---|---|---|---|---|
| PEI-RITC | 11.2 ± 5.3 | −32.1 ± 2.1 | — | — |
| Liposomes | 154.2 ± 13.6 | −40.2 ± 5.7 | 4.7 | 94.4 |
| PEG-PLGA NPs | 130.2 ± 9.4 | −16.5 ± 7.0 | 7.5 | 75.1 |
| PLGA NPs | 117.4 ± 18.2 | −23.6 ± 13.8 | 2.2 | 44.6 |

Example 3

Preparation and Characterization of PEI-RITC-Encapsulated Nanohybrids

It is highly desirable for a potential tumor-targeted delivery system to possess a size range of less than 200 nm in order to be able to passively accumulate into the tumor tissue. The size of the liposome-based system was controlled by extrusion using a membrane filter with pore size of 100 nm according to a slightly modified method previously described (Ko, et al. (2009) supra). For encapsulation into the polymeric NPs, the double emulsion method was chosen as it enables encapsulation of hydrophilic materials into a variety of polymers or copolymers with a controlled particle size (Perez, et al. (2001) supra; Vauthier & Bouchemal (2009) Pharm. Res. 26:1025-1058). As shown in Table 1, the encapsulation methods employed herein were successful in controlling the size, as particle sizes for all three nanohybrids were in the range of 100-150 nm. Both methods also showed relatively good loading efficiencies (45-94%) that correlate well with the reported values (Vauthier & Bouchemal (2009) supra). The zeta potential results indicated that the net surface charges on the NP- and liposome-based nanohybrids were all negative. This was expected since the carboxylic acid groups in PLGA and PEG-PLGA copolymers are deprotonated in neutral pH, and the phospholipid 1,2-dioleoyl-sn-glycero-3-phospho-(1'-rac-glycerol) (DOPG) is anionic (Panyam, et al. (2002) FASEB J. 16:1217-1226). The negative zeta potential values indicated that the encapsulation process in all formulations masked the positive charge on PEI-RITC. The controlled size, along with protection of positive charge from surface exposure, confirmed that the nanohybrid systems were had the desired characteristics (FIG. 1).

Example 4

Controlled Release of PEI-RITC-Encapsulated Nanohybrids

Figure 2:
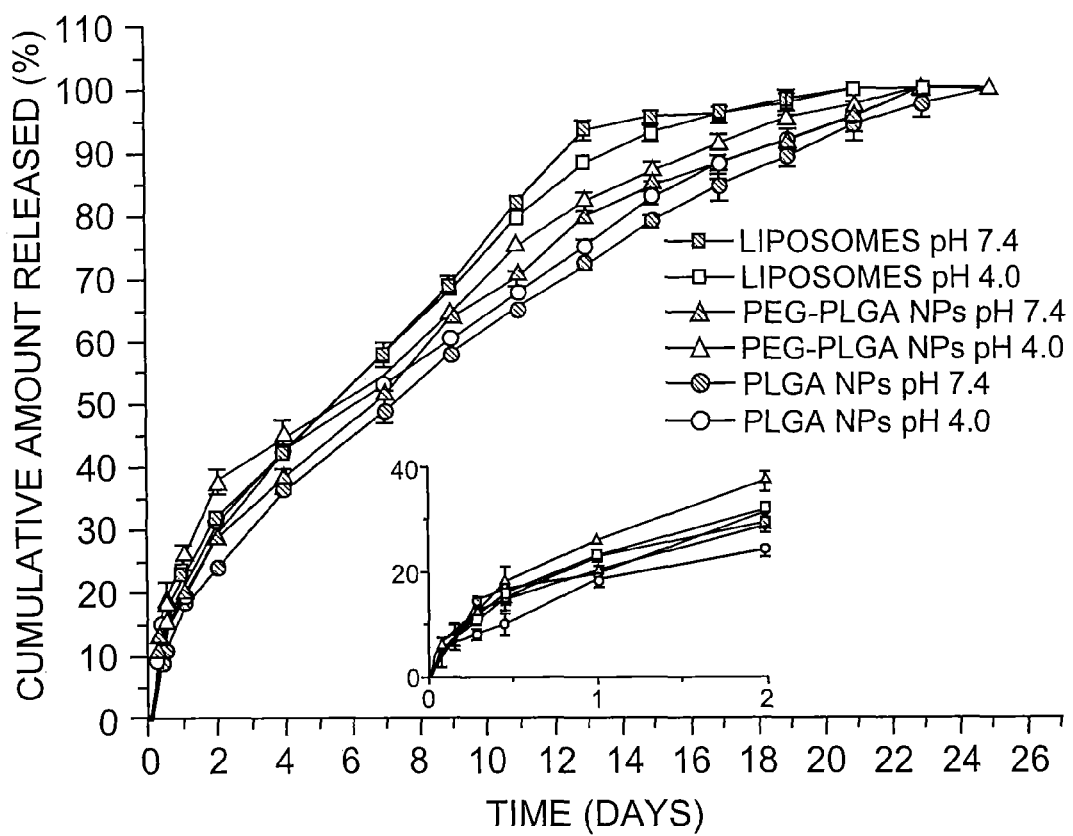
FIG. 2 shows release profiles of PEI-RITC from the three nanohybrids in PBS buffer with pH 7.4 and acetate buffer with pH 4.0 at 37° C. Little to no burst release was observed across all nanohybrids, with a sustained release profile up to 23 days. The overall release behavior was faster in pH 4.0 compared to pH 7.4 between the same type of nanohybrid formulation. The inset represents the zoomed-in release profiles for the first 2 days.

Given that the nanohybrid design was to temporally control cytotoxicity and cellular interactions through controlled release of the PEI conjugates, the release kinetics of PEI-RITC from the three nanohybrid systems was determined. The controlled release of PEI-RITC from the nanohybrids was studied by monitoring release profiles in buffers at pH 7.4 and 4.0 (FIG. 2). Polymeric NP-based nanohybrids showed slow, sustained release profiles that are typical of degradable polymers, without significant initial burst release. More than one mechanism contributing to drug release from polymeric NPs have been reported, for example, dissolution, surface desorption, diffusion through polymer pores or water-swollen polymer, and surface/bulk erosion of polymer matrix (Crotts, et al. (1997) J. Control. Release 47:101-111; Fu & Kao (2010) Expert Opin. Drug Del. 7:429-444; Polakovic, et al. (1999) J. Control. Release 60:169-177). Although no significant burst release effect was observed, the PEI-RITC release rate from PEG-PLGA and PLGA NPs was faster within the first 24 hours, which can be attributed to desorption of PEI-RITC that was located near the surface of the particles. Afterwards, the primary mechanism likely becomes diffusion through small channels formed from bulk degradation of the copolymers. PEG-PLGA NPs displayed a higher release rate compared to PLGA NPs, attributable to the hydrophilic nature of the PEG block, which facilitates water penetration and subsequent hydrolysis of the polymer (Penco, et al. (1996) Biomaterials 17:1583-1590; Avgoustakis, et al. (2002) J. Control. Release 79:123-135). As for the liposomes, release was faster within the first few hours, likely due to PEI-RITC adsorbed on or encapsulated near the liposome surface, followed by a sustained release behavior (Atyabi, et al. (2009) Acta Pharmaceut. 59:133-144). In addition, PEI-RITC release occurred faster in acidic pH than in pH 7.4 when comparing the same type of nanohybrid system, given that strongly acidic or basic environments can accelerate polymer degradation (Faisant, et al. (2006) *Int. J. Pharm.* 314:189-197).

Example 5

Kinetically Controlled Cytotoxicity of PEI-RITC-Encapsulated Nanohybrids

Figure 3A:
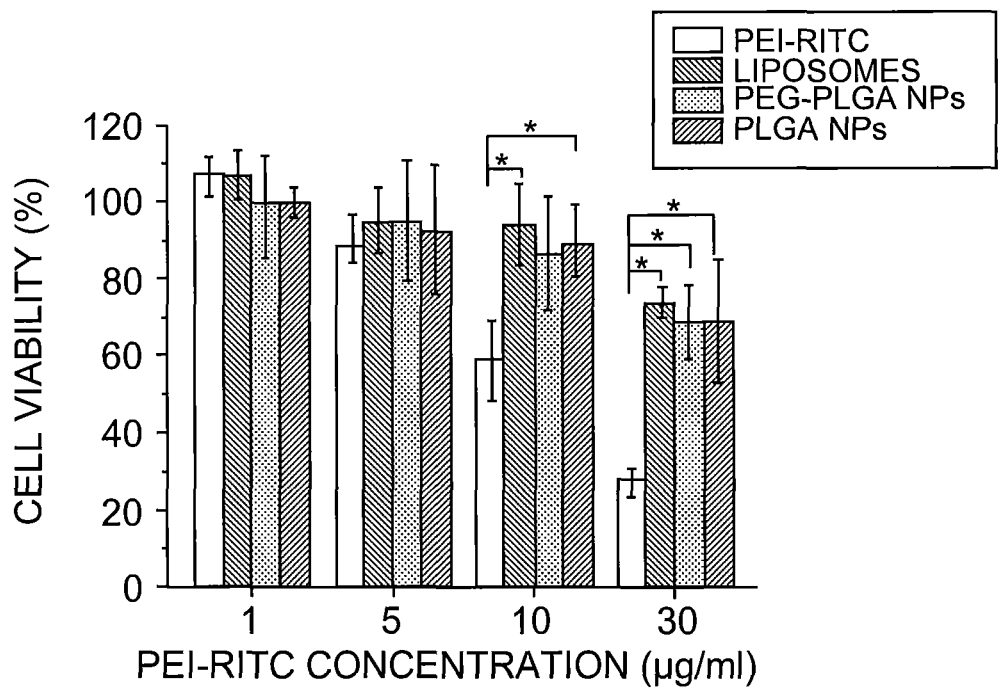
FIGS. 3A-3D show cytotoxicity of PEI-RITC and the three nanohybrids after incubation with MCF-7 cells for 1 hour (FIG. 3A), 4 hours (FIG. 3B), 24 hours (FIG. 3C), and 48 hours (FIG. 3D). PEI-RITC exhibited cytotoxicity in a concentration and incubation time dependent manner, whereas all nanohybrids showed a marked decrease in cytotoxicity kinetics. After 48 hours of treatment, all nanohybrids became comparatively toxic to PEI-RITC. * denotes statistical significance ($p<0.05$) between PEI-RITC and the three nanohybrids, based on a 1-way ANOVA followed by Tukey's post hoc test.
Figure 3B:
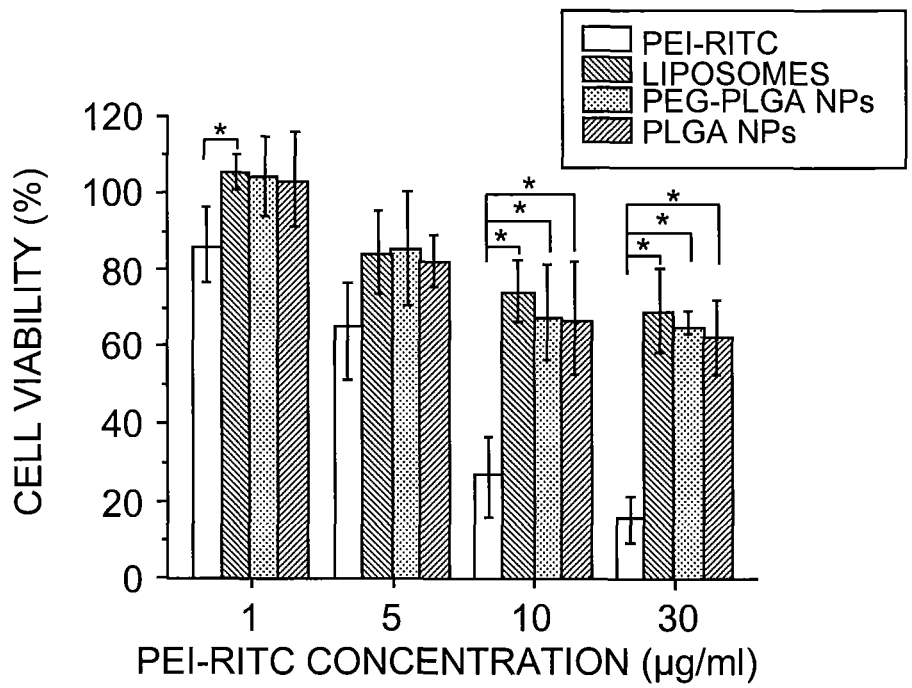
Figure 3C:
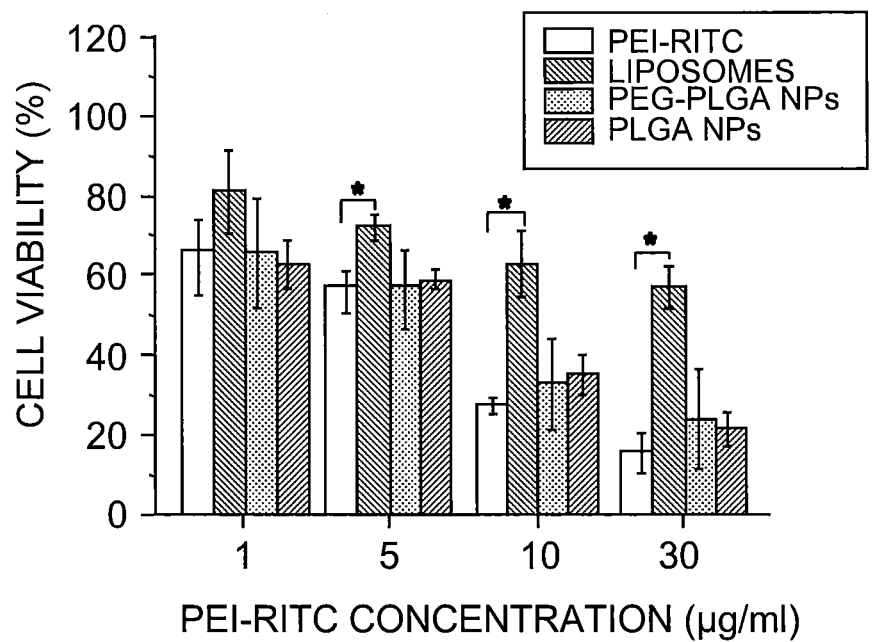
Figure 3D:
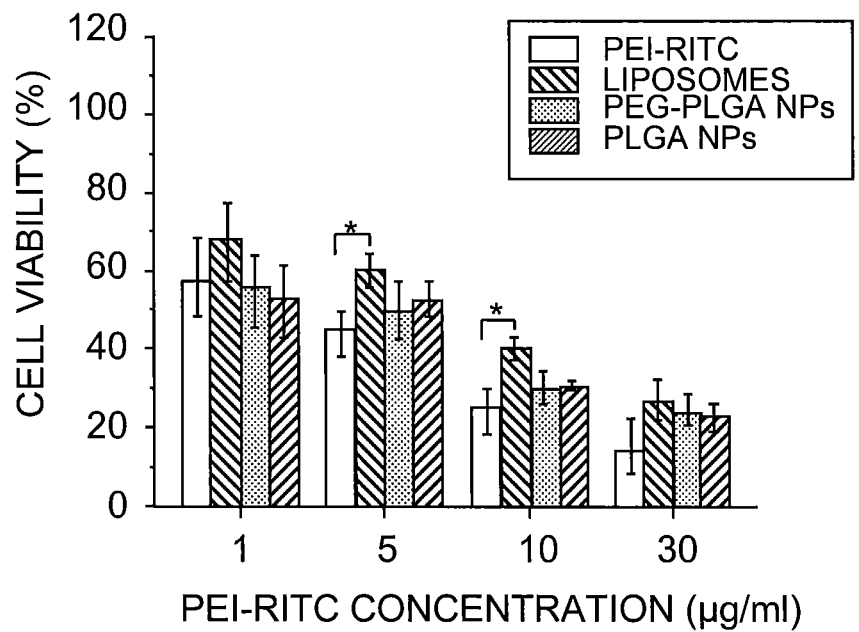

Although various mechanisms have been proposed, it is generally accepted that cellular internalization and cytotoxicity of cationic polymers are closely related to each other (Jevprasesphant, et al. (2004) *J. Control. Release* 97:259-267; Kopatz, et al. (2004) *J. Gene Med.* 6:769-776; Manunta, et al. (2006) *J. Immunol. Methods* 314:134-146; Seib, et al. (2007) *J. Control. Release* 117:291-300; Kitchens, et al. (2008) *Mol. Pharm.* 5:364-369). One of the proposed mechanisms of toxicity of cationic polymers has been described as being a consequence of nanoscale hole formation in the cell membranes (Hong, et al. (2009) supra; Hong, et al. (2004) supra; Hong, et al. (2006) *Bioconjugate Chem.* 17:728-734; Leroueil, et al. (2007) *Acct. Chem. Res.* 40:335-342). The nanoscale pores increased membrane permeability as observed by leakage of cytosolic enzymes and diffusion of small molecular probes into and out of cells. In this study, the cytotoxic concentration range of PEI-RITC and the three nanohybrids at extended incubation hours was investigated by determining the effect of PEI-RITC and the nanohybrids on the viability of MCF-7 cells. At earlier time points (1 and 4 hours, FIGS. 3A and 3B, respectively), the nanohybrids were significantly less toxic to MCF-7 cells than unencapsulated PEI-RITC, even at high PEI-RITC concentrations of 10-30 μg/mL. Note that it was previously shown that PEI at a concentration of >12 μg/mL causes significant cell death after 4 hours exposure to the cells (Hong, et al. (2006) supra). This temporal difference in inducing cytotoxicity can indirectly reflect the differences in rates of PEI-RITC release and internalization from those nanohybrids as compared to unencapsulated PEI-RITC. Within the first few hours of incubation, most of the PEI-RITC in the nanohybrids was still entrapped within either polymeric NPs or liposomes, which shield it from direct contact with cell membranes. As the incubation time increased, more PEI-RITC was released, which in turn increased the amount of PEI-RITC in direct contact with cells, rendering them more susceptible to its toxicity. After 48 hour incubation, however, all nanohybrids exhibited similar cytotoxicity (FIG. 3D), indicating that PEI-RITC was almost completely released, internalized into the cells, and induced cytotoxicity. Alternatively, this may have been due to the proliferation of residual viable cells, which caused the cytotoxic effects of PEI to even out. Interestingly, among the three nanohybrids, the liposome-based nanohybrid showed the most protective effect against PEI-RITC toxicity, particularly after 4 and 24 hours (FIGS. 3B and 3C). This may be attributed to the difference in the internalization mechanism between liposome- and polymeric NP-based systems, since cell internalization of liposomes may occur through endocytosis, membrane fusion, and other mechanisms (Torchilin (2005) supra), allowing them to transfer PEI-RITC without direct contact with the cell membrane.

Example 6

Kinetic Control over Cellular Uptake of PEI-RITC-Encapsulated Nanohybrids

Figure 4:
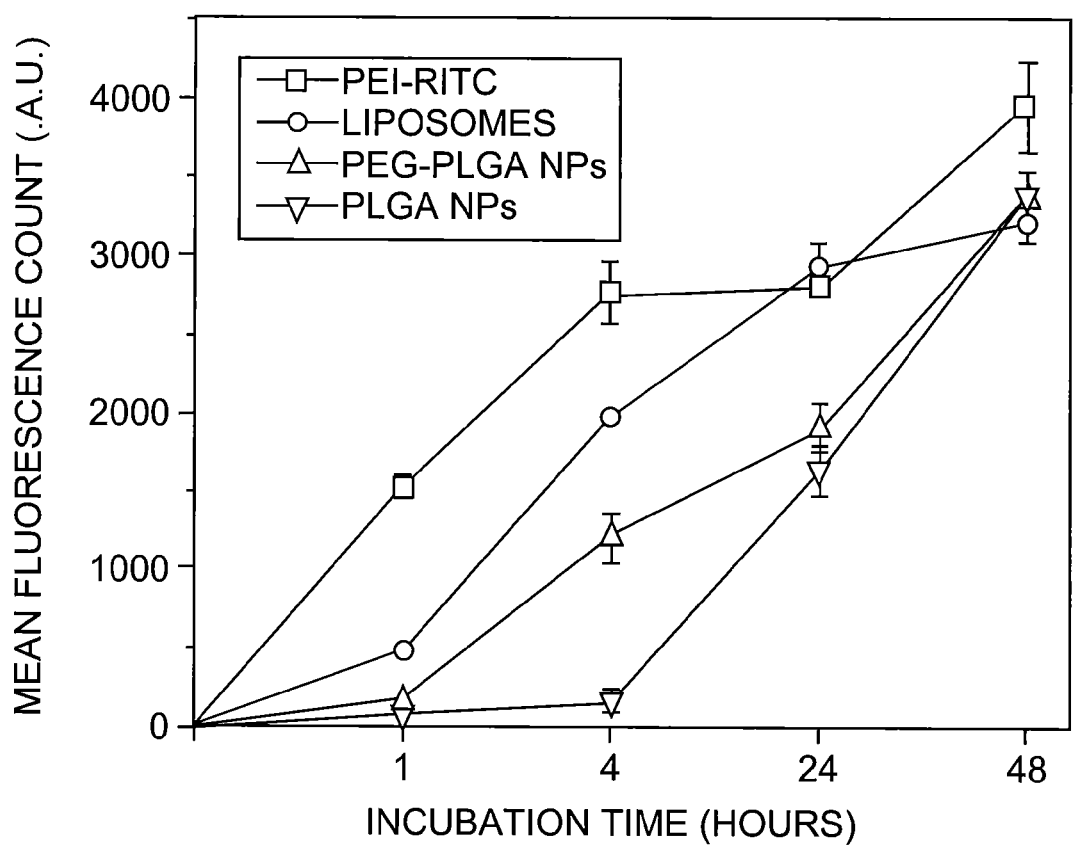
FIG. 4 shows mean fluorescence following treatment of MCF-7 cells with PEI-RITC and the three nanohybrids at a concentration of 0.5 μg/ml based on PEI-RITC up to 48 hours. Kinetic control over PEI-RITC internalization was further confirmed as unencapsulated PEI-RITC showed the fastest uptake, as indicated by having the highest fluorescence count compared to the three nanohybrid formulations. Cell binding and uptake of the nanohybrids occurred in the order of liposomes, PEG-PLGA NPs, and PLGA NPs, which was consistent with the confocal data.

Subsequently, it was determined how the controlled release of PEI-RITC and the type of the protective layers (either polymeric NPs or liposomes) affect the rate of cellular uptake of the nanohybrids. Throughout this particular study, a low concentration of PEI-RITC and the three nanohybrid systems was used (0.5 μg/mL based on PEI-RITC) to assure that the observations were a result of non-cytotoxic interactions between the nanomaterials and cells, as opposed to cell death. Images obtained using confocal laser scanning microscopy (CLSM) qualitatively revealed that the fastest uptake was observed for unencapsulated PEI-RITC, followed by, in order, liposomes, PEG-PLGA NPs, and PLGA NPs. Red, green, and blue fluorescence channels were respectively from PEI-RITC, cell membranes stained by WGA-AF488 conjugate, and nuclei stained by DAPI. The CLSM observation was further supported by quantitative results using a fluorescence activated cell sorter (FACS). As shown in FIG. 4, following incubation up to 24 hours, and in accordance with the CLSM images, the average fluorescence was highest for unencapsulated PEI-RITC, followed by liposomes, PEG-PLGA NPs, and PLGA NPs. After 48 hours of incubation, all of the materials (PEI-RITC and the three nanohybrids) displayed similar fluorescence intensities, which was consistent with the cytotoxicity (FIG. 3) and confocal data. The fast uptake of PEI was not surprising as PEI is known to spontaneously interact with cells via adsorption on the cell surface and internalization into the cells (Hong, et al. (2006) supra). It has been suggested that the biodegradable NPs do not enter cells but rather deliver their cargo via extracellular release or contact-based transfer (Chen, et al. (2008) *Proc. Natl. Acad. Sci. USA* 105:6596-6601; Xu, et al. (2009) *Mol. Pharm.* 6:190-201). This could explain the slow kinetics in PEI-RITC uptake from polymeric NPs observed in the instant study, since the NP-based nanohybrids would have to go through polymer degradation, release, and subsequent internalization of PEI-RITC into the cell. As for the liposome-based nanohybrid system, liposomes exhibited slowest cytotoxicity kinetics (FIG. 3), and yet fastest cellular uptake kinetics among the three nanohybrid systems (FIG. 4). This set of observations indicated that, unlike the NP-based nanohybrids, cellular internalization of PEI-RITC upon release was not the only mechanism for cell entry of the liposome-based nanohybrid. In fact, upon adsorption onto the cell surface, it was previously reported that liposomes internalize into the cell through membrane fusion and/or endocytosis (Torchilin (2005) supra). The co-existence of the internalization mechanisms likely allows relatively fast uptake kinetics with reduced cytotoxicity at early time points. Even though they displayed similar release kinetics in buffer, PLGA NPs had a much slower uptake rate than their PEG-PLGA counterparts. Significant uptake of PLGA NPs was only observed after 24 hours, with complete internalization after 48 hours. This was again probably due to the hydrophobic nature of the PLGA copolymer, which impedes degradation and subsequent PEI-RITC release (Avgoustakis, et al. (2002) supra). The presence of the cellular environment accentuated the difference between the two types of polymeric NPs, with PEG-PLGA NPs displaying an intermediate uptake rate between the liposome- and PLGA-based nanohybrids. The PEG-PLGA NPs started to show red signals after 4 hours of incubation, with complete internalization within 24 hours. Although the results indicates that the PEI-RITC internalization from the polymeric NPs was largely dependent upon the degradation and release profiles, it should be noted that other mechanisms such as endocytosis of the whole NPs may co-exisit (Vasir & Labhasetwar (2007) *Adv. Drug Deliver. Rev.* 59:718-728). As seen in FIG. 2, degradation of NP-based nanohybrids may not occur within 2 days, and the red fluorescence observed in the CLSM images may partially come from the nanoparticles that have been associated with the cells as an intact form. However, it was obvious that the release kinetics in buffer did not follow the same order or rate observed in the cytotoxicity or the cellular uptake studies (FIGS. 2 and 3). This could be explained by the difference in the microenvironment surrounding the nanohybrids. For the release test shown in FIG. 2, all three formulations were suspended in either PBS or acetate buffer only, making the environment markedly different than in the presence of cells, as in the subsequent cytotoxicity and cell uptake experiments (FIGS. 3 and 4). Due to the presence of enzymes and proteins, as well as the difference in cellular uptake mechanisms, the differences in release kinetics across the nanohybrids were more accentuated when compared to the release in buffers.

The instant analysis established kinetic control over cytotoxicity and cellular interactions of PEI. When incorporating active drug compounds, which are covalently linked to the primary amine groups of PEI, the physicochemical and biological behavior of the system is expected to be very similar to PEI, since the presence of RITC molecules on PEI also serves as a model for small molecule drugs. As for complexation with genetic materials, which lowers net positive charges, overall toxicity of PEI would likely be reduced (Kunath, et al. (2003) *J. Control. Release* 89:113-125; Zhao, et al. (2009) *Biol. Pharm. Bull.* 32:706-710). Moreover, the presence of genetic material will also likely affect the overall particle size of the nanohybrid systems. However, with optimization of the encapsulation process, fine control over the size is obtainable. Furthermore, given that PEI is known to spontaneously interact with cells, facilitating cellular entry (Hong, et al. (2006) supra; Neu, et al. (2005) *J. Gene Med.* 7:992-1009; Fischer, et al. (2003) *Biomaterials* 24:1121-1131), it offers an excellent model system for multifunctional vectors without preparation of complex structures with cytotoxic drugs and targeting agents.

Example 7

Targeting Efficacy of the Nanohybrid Composition

To validate the enhanced targeting efficacy using the instant nanohybrid composition, in vitro experiments can be performed. The passive targeting due to EPR effect can be tested on a microfluidic system integrated with PEG hydrogel, and active targeting can be tested using cell culture.

In Vitro Tests of Passive Targeting Efficacy Due to EPR Effect. Microfluidic channels and tubing are integrated with PEG hydrogel to mimic the blood circulating near the tumor site, modeling the leaky nature of the vasculature. To be similar to blood vessels, the inner surface of the microfluidic channels are silanized and coated with a monolayer of neutral phospholipid, 1,2-Dilauroyl-sn-glycero-3-phosphocholine (DLPC). The porosity and pore size of the PEG hydrogel can be controlled using PEG-diacrylate (PEGDA) with various DA contents, leading to various crosslinking densities upon UV curing. The resulting hydrogels can be characterized, and the relationship between porosity/pore size and diffusion of the nano-hybrid systems is established. The device is used to test whether the nanoparticles with controlled size distribution can accumulate specifically at the "tumor" site. The accumulation and diffusion can be quantitatively measured by using a fluorescence microscope In Vitro Tests of Active Targeting Efficacy. The instant nanohybrid composition can tested in vitro to ensure that the nancore sustains biologically active properties after encapsulation. The active targeting and treatment efficacy of the nanohybrid composition can be compared with control groups, which are (1) polymer nanoparticles with encapsulated chemotherapeutic drugs and fluorophores—no nanocores (passive targeting only); (2) nanocores with targeting molecules, drug, and fluorophores; and (3) a negative control group (saline, nanoparticles without drugs, targeted nanocores without drug, nanohybrid compositions with the targeted nanocores but without drugs). To test in vitro efficacy of the nanohybrid composition, fluorescence activated cell sorter (FACS) and confocal laser scanning microscopy (CLSM) can be employed to investigate release kinetics of the encapsulated nanocores and subsequent specificity and binding/uptake efficiency of the released nanocores. The fluorophores conjugated to the nanocores enable the use of fluorescence-based analytical techniques. Examples of tumor cell lines include KB (FR+/−) for FA targeting. For the FA-based targeting, the KB cell line can be purchased from the American Type Tissue Collection (ATCC, Manassas, Va.) and be grown continuously as a monolayer at 37° C. and 5% $CO_2$ in RPMI 1640 medium (Mediatech, Herndon, Va.), resulting in FR down-regulated KB (FR− KB). The RPMI 1640 medium can be supplemented with penicillin (100 units/ml), streptomycin (100 mg/ml), and 10% heat-inactivated fetal bovine calf serum (FBS) before use. FR over-expressing KB cells (FR+ KB) can be cultured in RPMI 1640 medium without folic acid (Mediatech) for at least 4 days before experiments.

These experiments are expected to demonstrate that nanoparticles with controlled size distribution will selectively accumulate at the leaking site and slowly diffuse through the hydrogel. Moreover, it is expected that nanohybrid composition will not interact with the cells until the shell degrades and releases the nanocores and once the nanocores are released, cells that over-express the FR will selectively interact with the nanocores (no or very low interaction with FR− KB). Furthermore, the drugs conjugated to the nanocores will act as a pro-drug (no toxic effect) until the conjugation bond is cleaved by enzymatic activities of the cells after endocytosis of the nanocores. In addition, the cells (FR+ KB only) will be killed by the cleaved drugs.

Example 8

Flash NanoPrecipitation to Produce Drug-Loaded Polymeric Nanoparticles

This example analyzes the fundamental mechanisms of self-assembly to produce nanoparticles using a multi-inlet vortex mixer (MIVM). An amorphous copolymer poly(ethylene oxide)-b-poly(styrene) (PEO-b-PS), a semicrystalline copolymer poly(ethylene oxide)-b-poly(ε-caprolactone) (PEG-b-PCL), and an ionic copolymer poly(ethylene oxide)-b-poly(acrylic acid) (PEG-b-PAA) were used to produce nanoparticles encapsulating a small hydrophobic molecule, β-carotene, and cationic macromolecule, polyethyleneimine (PEI). The dependence of the nanoparticle sizes on Reynolds number, supersaturation rate, nature of polymers, drug loading rate, and the type of interaction forces was studied. Mixing patterns in the MIVM were imaged by a light microscope.

Materials. Poly(ethylene oxide)-b-poly(ε-caprolactone) (PEG-b-PCL) (MW 5000-b-3600) and poly(ethylene oxide)-b-poly(acrylic acid) (PEG-b-PAA) (MW 6000-b-2000) were purchased from Polymer Source (Dorval, Canada). Poly(ethylene oxide)-b-poly(styrene) (PEO-b-PS) (MW 1000-b-3000) was provided by Goldschmidt GmbH (Essen, Germany). β-carotene (95.0% purity), iodine, potassium iodide, tetrahydrofuran (THF), potassium thiocyanate, iron (III) nitrate and branched poly(ethyleneimine) (MW 750,000)

were purchased from Sigma-Aldrich (St Louis, Mo.). Unless otherwise stated, all chemicals were purchased at standard grades and used as received.

Mixing and Flow Pattern Visualization. Iron nitrate and potassium thiocyanate were used to image the mixing process in the MIVM. The reactor and channel height was 1.53 mm. The inlet channel width was 1.19 mm. The reactor diameter was 6.26 mm, and the outlet diameter was 1.40 mm. To observe flow patterns in the MIVM composed of dilute solutions and suspensions as the conditions of making nanoparticle suspensions, inorganic dyes were used instead of organic dyes. Organic dyes may affect the properties of aqueous solutions when dissolved at the concentrations sufficient for visualizing flow patterns in the MIVM (Tice, et al. (2003) *Langmuir* 19(22):9127-9133). Digitally controlled syringe pumps (Harvard Apparatus, PHD 2000 programmable, Holliston, Mass.) were integrated with the MIVM to accurately control the flow rates of the inlet streams. The solution from stream 1 and stream 3 was 1 wt % iron nitrate dissolved in DI water. The solution from stream 2 and stream 4 was 1 wt % potassium thiocyanate dissolved in DI water. Mixing of iron nitrate and potassium thiocyanate generated red precipitation of iron thiocyanate.

The four inlet streams had the same volumetric flow rate. Flow patterns in the center of the chamber, 6 mm in diameter, were observed under a microscope (American Scope, IN200A-P, Chino, Calif.) with an objective of 4× magnification and a digital microscope camera (Motic, Moticam 1000, Xiamen, China) coupled to an image analysis software (Motic images plus 2.0). The exposure time was 30 ms.

Nanoparticle Preparation and Characterization. Nanoparticles of β-carotene encapsulated in two block copolymers, PEO-b-PS (MW 3000-b-1000) and PEG-b-PCL (MW 5000-b-3600), were generated in the MIVM by hydrophobic interaction. For each copolymer used, stream 1 and 2 had the same volumetric flow rate. Stream 3 and 4 had the same volumetric flow rate, which was varied from 1 to 9 times the flow rate of stream 1 and 2 to obtain different supersaturation values. For nanoparticles of β-carotene encapsulated in PEO-b-PS (Mw 3000-b-1000), the solution from stream 1 was 1 wt % β-carotene dissolved in THF. The solution from stream 2 was 1 wt % PEO-b-PS (Mw 3000-b-1000) dissolved in THF. The other two streams were DI water. For nanoparticles of β-carotene encapsulated in PEG-b-PCL (MW 5000-b-3600), the solution from stream 1 was PEG-b-PCL (MW 5000-b-3600) with various concentrations from 1 wt % to 5 wt % and 1 wt % β-carotene dissolved in THF. The other three streams were DI water.

Nanoparticles of branched PEI (MW 750,000) encapsulated in PEG-b-PAA (MW 6000-b-2000) were generated in the MIVM by electrostatic interaction. The solution from stream 1 was 1 wt % (or 2 wt %) PEG-b-PAA (MW 6000-b-2000) dissolved in water. The solution from stream 2 was 0.43 wt % (or 0.86 wt %) PEI (MW 750,000) dissolved in water. The concentration was designed to have equal positive and negative charges. The other two streams were DI water. The volumetric flow rates of stream 1 and stream 2 were kept equivalent. The volumetric flow rates of stream 3 and stream 4 were kept equivalent and four times of that of stream 1 and stream 2.

Nanoparticle sizes and size distribution were measured by dynamic light scattering (DLS) (Agilent, 7030 Nicomp DLS/ZLS-size and zeta, Santa Clara, Calif.). The particle sizes were reported as the intensity-weighted radius $a_h$, where $$a_h \propto \sum_{k=1}^{max,\infty} n_k a_k^6 \bigg/ \sum_{k=1}^{max,\infty} n_k a_k^5.$$

$a_k$ was the radius of particle k, and $n_k$ was the number of particles at a given size.

The images of the particles were taken by using a transmission electron microscope (TEM) (JEOL Ltd., JEM-3010, Tokyo, Japan) operated at 300 kV. The sample of β-carotene encapsulated in PEG-b-PCL was prepared by placing 30 microliters of the suspension on a formvar grid. After 30 minutes, 20 microliters of 2% phosphotungstic acid (PTA) ($H_3PO_4$ $12WO_3.24H_2O$) (pH 6.9) was added to negatively stain the sample. Staining lasted for 2 minutes before PTA was removed by the filter paper. Detailed procedure of staining organic nanoparticles for TEM images can be found in the literature (Lavasanifar, et al. (2001) *J. Contr. Rel.* 77(1-2): 155-160). The sample was dried for 4 hours before taking the TEM images. The images of β-carotene particles without protection of polymers were taken as a comparison to the nanoparticles. Thirty microliters of the sample was placed on a membrane-coated carbon grid and dried for 4 hours prior to imaging. For both cases, the concentration of β-carotene was 0.1 wt %.

The encapsulation rate and drug loading rate (DLR) of β-carotene in block copolymers was characterized by sequential processes of filtration, freeze-drying, re-dissolving, and UV-Vis measurements. The encapsulation rate was calculated from the expression, $$\text{Encapsulation rate (\%)} = \frac{\text{Amount of } \beta\text{-carotene encapsulated in nanoparticles}}{\text{Feeding amount of } \beta\text{-carotene}} \times 100\%.$$

The drug loading rate (DLR) was calculated from the expression, $$DLR = \frac{\text{mass } \beta\text{-carotene encapsulated}}{\text{total mass of nanoparticles}} \times 100\%.$$

The nanoparticles of β-carotene encapsulated in PEG-b-PCL were generated by using the MIVM and collected in a big reservoir of water (~100 times the dilution rate) to quench the reaction and prevent the fast growth of particle size due to Ostwald ripening. The nanoparticle suspensions were filtered through a 0.45 μm filter (VWR, 0.45 μm Polyethersulfone filter, West Chester, Pa.). β-carotene that was not encapsulated in the nanoparticles would form large crystals and be filtered out of the suspension. After the filtration, the nanoparticles were freeze-dried by using a freeze dryer (LABCONCO, FREEZONE 6 liter console, Kansas City, Mo.) for 3 days. The nanoparticles were then re-dissolved in THF. The encapsulation rate and DLR of β-carotene was quantified by using a UV-Vis spectrophotometer (Beckman Coulter, DU800 UV/Visible spectrophotometer, Brea, Calif.). The absorbance was measured at a wavelength of 310 nm. Various drug loading rates were achieved by changing the weight ratio of β-carotene to PEG-b-PCL from 1:1 to 1:5.

Critical Micelle Concentration (CMC) Measurements. Critical micelle concentration (CMC) of the diblock copolymers in water and THF mixed solvent was measured by using both the Baleux assay method and the light scattering method. PEG-b-PCL was dissolved in water and THF mixed solvent and agitated by using a vortex mixer (Boekel, 270100 Tap Dancer-Vortex Mixer, Feasterville, Pa.). The concentration of PEG-b-PCL was much higher than the CMC of PEG-b-PCL to ensure the formation of PEG-b-PCL micelles. Solution of PEG-b-PCL in mixed solvent was pipetted into 100K Molecular Weight Cut Off centrifuge tubes (Pall, 100K Nanosep Centrifugal Devices, Port Washington, N.Y.) and centrifuged by a centrifuge (Fisher Scientific, Marathon 16 KM microcentrifuge, Pittsburgh, Pa.) at 14000 g for 15 minutes. The concentration of PEG-b-PCL in the mixed solvent through the membrane after centrifuge was considered as the CMC. Iodine-potassium iodide solution was made of 0.03 grams of iodine and 0.06 grams of potassium iodide in 3 milliliters of DI water. The solution was kept in a brown glass bottle no longer than 8 days. 0.05 milliliters of the iodine-potassium iodide solution was then added to 2 milliliters of PEG-b-PCL solution. The light absorbance was measured by a UV-Vis spectrophotometer (Shimadzu, UV-1601, Kyoto, Japan) at a wavelength of 500 nm. The Baleux assay method (Baleux (1972) *CR Acad. Sci. Ser. C* 279:1617-1620) was only used on the samples of THF to water ratio equal to or less than 10%, because at a higher THF ratio, the light absorbance was influenced by the organic solvent. The light scattering method (Johnson BK (2003), Princeton University, Princeton, N.J.) was also used to analyze the CMC of PEG-b-PCL in water and THF solvent mixture. Various concentrations of PEG-b-PCL in solvent mixture were prepared and the CMC was identified by the jump in light scattering when micelles formed.

Effect of Flow Field and Reynolds Number: Starting the Competitive Kinetics Simultaneously. Flash NanoPrecipitation is a process of kinetic control instead of thermodynamic equilibrium which constrains the drug loading rate and causes broad size distribution and low stability as in most other processes, such as emulsion and traditional precipitation. At thermodynamic equilibrium, drug loading is driven by entropy of mixing of the drug with the hydrophobic core of the micelle. Based on Flory-Huggins theory and Chi mismatch, drug loading is disfavored (Ugelstad, et al. (1992) *Progress in Polymer Science* 17 (1):87-161). The kinetic control of Flash NanoPrecipitation overcomes the drug loading limit.

High Reynolds number homogenous mixing was essential to start the competitive processes of organic solute nucleation and growth as well as polymer aggregation simultaneously and uniformly, which provided control over drug loading rate and uniform particle size distribution. However, the appropriate definition of Reynolds number is not obvious for a system with multiple inlet streams of solutions with various velocities, dimensions, and viscosities like the MIVM. Regression modeling on data from previous MIVM research was used to develop an optimal formulation of Reynolds number (Re) as (Russ, et al. (2010) *Chemical Engineering Communications* 197 (8)), $$Re = \left[\sum_i \left(\frac{Q_{base}}{Q_{acid}}\right)\left(\frac{Q_i}{Q_{total}}\right)Re_i^{2/3}\right]^{3/2}, \quad (1)$$

where $Q_{base}$, $Q_{acid}$, $Q_{total}$, and $Q_i$ represented the total volumetric flow rate of the base streams, the acid streams, the total volumetric rate of all streams, and flow rate of stream i, respectively. $Re_i$ was the Reynolds number of the ith inlet stream calculated by the average velocity, viscosity, and dimension of the inlet stream. However, to be comparable to a previous simulation and experimental results, the definition of Re in this study was, $$Re = \sum_{i=1,N} V_i L/\nu_i, \quad (2)$$

where $V_i$ was the velocity of the ith inlet stream, L was the chamber diameter, $\nu_i$ was the kinematic viscosity of the ith inlet stream, and N=4 was the number of inlet streams.

Flow patterns inside an MIVM at various Re were visualized by mixing the streams of $Fe(NO_3)_3$ with KSCN to form inorganic complex $Fe(SCN)_x^{(3-x)+}$ (x~3, absorption maximum $\lambda_{max}$~480 nm, extinction coefficient $\epsilon$~$5\times10^3$ cm$^{-1}\cdot$M$^{-1}$). The inorganic dye was chosen because of its Newtonian behavior. The viscosity of the solution of the complex was 1.08±0.05 mPa·s at the imaging concentration (<0.067 M) (Tice, et al. (2003) *Langmuir* 19 (22):9127-9133). The viscosity of the two colorless streams of $Fe(NO_3)_3$ (<0.067 M) and KSCN (<0.2 M) was 1.00±0.05 mPa·s (Tice, et al. (2003) supra). At the mixing front, the red precipitation of iron complex $Fe(SCN)_x^{(3-x)+}$ indicated the streamlines. With higher Re, flow had more circulation and streamlines were closer. Eventually diffusion across the streamlines was fast enough to make the mixing in the MIVM homogeneous. At low Re, the mixing time, $\tau_{mix}$, was given by, $$\tau_{mix} = l^2/2D \quad (3)$$

where D (m$^2$/s) was the diffusion constant and l was the striation length, the distance over which mixing could occur by diffusion. For a molecule with a diffusion constant of D=$10^{-9}$ m$^2$/s, reducing l from 100 μm to 1 μm decreases $\tau_{mix}$ from 5 s to 0.5 ms. The images showed that increasing Re enhanced mixing by reducing the striation length. At Re over 1400, the red precipitation of $Fe(SCN)_x^{(3-x)+}$ was homogenous in the mixer under the microscope. Results from numerical simulation and experimental analysis using competitive reactions revealed that adequate micromixing was obtained with Re over 1600 (Liu, et al. (2008) *Chemical Engineering Science* 63 (11):2829-2842).

Similar to previous results from numerical simulation (Liu, et al. (2008) supra), the transition of particle size happened at Re near 2000. With higher Re, the mixing was more homogeneous and effective. Over the critical Re (~2000), the flow was fully developed turbulence and the resulting particle sizes were not sensitive to the flow field. At low Re (Re<2000), nanoparticle sizes increased with the decrease of Re, while nanoparticle sizes decreased with the decrease of Re. This opposite transition was because of the different interaction forces between the encapsulated model drugs and diblock copolymers. The interaction between β-carotene and PEO-b-PS or PEG-b-PCL was hydrophobic interaction. The nanoparticle sizes depended on the competitive kinetics of polymer aggregation and β-carotene nucleation and growth. At lower Re, β-carotene and polymers were not homogeneously mixed, so that locally there were not sufficient polymers nearby to terminate the growth of β-carotene. Therefore, the nanoparticle sizes were larger compared to the nanoparticles formed at higher Re. The interaction between positive-charged PEI and negative-charged PAA block of PEG-b-PAA was an electrostatic interaction. At low Re, negative-charged PEG-b-PAA had less chance to interact with positive-charged PEI and nanoparticles were smaller compared to those generated at higher Re. At high Re (Re>2000), the MIVM provided adequate micromixing. Nanoparticle sizes no longer depended on Re or the flow field.

High Re homogeneous mixing was also critical for obtaining high drug encapsulation rate. The limited drug encapsulation from thermodynamic equilibrium could be discerned from the curves of solubility boundaries for organic solute and polymers as a function of anti-solvent addition. The solubility of β-carotene as a model hydrophobic drug and CMC of two diblock copolymers, PEO-b-PS and PEG-b-PCL, as a function of THF content at room temperature was determined. Gradual anti-solvent addition involved traversing the operating line from the initially pure solvent condition to the intersection first with the solubility curve of β-carotene and then with the CMC curves of the diblock polymers as the stabilizer. At the point when the operating line crossed the solubility curve of β-carotene, β-carotene would begin to precipitate as unprotected crystals until more anti-solvent was added and polymers started aggregation. However, when the operating line intersected with the CMC curves of polymers, more than 70% of β-carotene had precipitated and grew to be large crystals, which would be filtered out of the suspension. Not only this was a waste of the active compound, but drug encapsulation rate in the nanoparticles was also low. In the process of Flash NanoPrecipitation, homogeneous mixing could be reached in milliseconds to produce high levels of supersaturation for β-carotene as well as polymers at final solvent composition. The composition of the resulting nanoparticles was decided by the stoichiometry of the feeds instead of the partition coefficient of the drug with polymers. Therefore, polymeric nanoparticles with higher drug encapsulation rate were possible. When nanoparticles were generated at high Re in the MIVM, the encapsulation rate of β-carotene in block copolymers was higher than 85%.

Effects of Supersaturation Rate and Nature of Polymers. Supersaturation rate directly affected the nucleation and growth time of the organic solute and polymer aggregation time. The rate of nucleation, J, was estimated by the primary homogeneous nucleation rate (Dirksen & Ring (1991) *Chemical Engineering Science* 46 (10):2389-2427), $$J \propto \exp\left[-\frac{16\pi\gamma^3 \upsilon^2}{3k_B^3 T^3 (\ln S)^2}\right], \quad (4)$$

where γ was solid-liquid interfacial tension and υ was molar volume of the solute. S was the supersaturation ratio defined as, $$S = c(r)/c^* \quad (5),$$

where c(r) denoted the solubility of a particle with radius r and c* was the equilibrium solubility. The rate for primary homogenous nucleation was derived by assuming that, for supersaturated solutions, solute molecules combined to produce embryos. Quasi-equilibrium developed between molecules and embryos, with a corresponding distribution of free energy due to the formation of a new volume and new surfaces. The nucleation rate calculated from Equation 4 could be orders of magnitude different from experimentally measured rates, but the derivation captured the general features of particle formation (Dirksen & Ring (1991) supra). By adopting homogeneous primary nucleation kinetics, the rate of block copolymer self-assembly was approximated by using Equation 4 and inserting the value for supersaturation, S, defined as the ratio of polymer concentration over CMC. However, most primary nucleation in practice was likely to be heterogeneous nucleation, since supersaturation for homogeneous nucleation was much higher than heterogeneous nucleation. Heterogeneous nucleation could be estimated by using the same equation, but the surface energy of the solid-liquid interface was replaced by the surface energy of the solid-foreign surface interface. There are two proposed mechanisms to explain the effects of supersaturation on size distributions of organic particles protected by block copolymers. In one scenario, nucleation started as homogeneous nucleation of β-carotene, since β-carotene had higher supersaturation rate and therefore higher nucleation rate. Polymers then began to assemble on the surfaces of the particles and finally arrested the particle growth. In another scenario, hydrophobic sites on the polymers could have served as the nucleation seeds. Nucleation then started as heterogeneous nucleation, and particle growth stopped when polymer aggregation was terminated by the combined effects of particle dilution and steric hindrance of the hydrophilic block of the copolymer. With either mechanism, at higher supersaturation, more nucleation sites were generated and nanoparticles were smaller.

In this study, β-carotene and diblock copolymers were dissolved in THF and mixed with DI water as an anti-solvent. Different supersaturation rates were generated by varying the ratio of THF and DI water. In experiments, by varying THF and water ratio from 1:1 v/v to 1:5 v/v, the supersaturation was changed more than 100 times for β-carotene (from 12 to 1489). However, supersaturation rates for PEO-b-PS and PEG-b-PCL remained at about 20 and 5, respectively. Regardless of Re, nanoparticles of 50 nm to 500 nm could be produced by changing supersaturation rates.

The long-term stability of the nanoparticles depended on polymer nature and solvent composition. At the same supersaturation rate of β-carotene, nanoparticles protected by PEO-b-PS were smaller than those protected by PEG-b-PCL. Extensive studies (Mao, et al. (2006) *Bioconjugate Chemistry* 17 (5):1209-1218; Kwon (2003) *Critical Reviews in Therapeutic Drug Carrier Systems* 20 (5):357-403; Lin, et al. (2003) *Pharmaceutical Research* 20 (4):668-673; Photos, et al. (2003) *Journal of Controlled Release* 90 (3):323-334; Mosqueira, et al. (2001) *Pharmaceutical Research* 18 (10): 1411-1419; Lee, et al. (1999) *Bioconjugate Chemistry* 10 (6):973-981) have confirmed that the density of the coverage and the chain length of PEG influence the stability of the nanoparticles. In general, a longer PEG chain provides a higher energy barrier to prevent nanoparticles from coagulation and degradation. It has also been found that the hydrophobic core may also affect the long-term stability of the nanoparticles (Monkenbusch, et al. (2000) *Physica B-Condensed Matter* 276:941-943). Stability of PEO-b-PS nanoparticles encapsulating hydrophobic compounds has been discussed and reported in the literature (Mullin (1993) Crystallization. 3rd edn. Butterworth Heinemann, Oxford, UK; Liu, et al. (2007) *Physical Review Letters* 98 (3)). PCL, which is biocompatible and biodegradable, has many applications in drug delivery (Geng & Discher (2005) *Journal of the American Chemical Society* 127 (37):12780-12781; Shuai, et al. (2004) *Journal of Controlled Release* 98 (3):415-426; Shuai, et al. (2004) *Bioconjugate Chemistry* 15 (3):441-448). However, the instability of PEG-b-PCL micelles and nanoparticles has been observed. One proposed mechanism was that low Tg PCL chains were sufficiently mobile on the surface and they could rearrange and begin to crystallize (Monkenbusch, et al. (2000) supra). The lamella morphology of PCL crystal phase would allow aggregation into larger lamella structures.

Solvent composition affected long-term stability of nanoparticle suspensions by Ostwald ripening (Mullin (1993)

supra; Liu, et al. (2007) supra). The diffusion-controlled growth kinetics was given by ripening (Mullin (1993) supra; Liu, et al. (2007) supra), $$\frac{dr}{dt} = \frac{\gamma v^2 D_{drug} c^\infty}{3RTr^2},\qquad(6)$$

where $D_{drug}$ and $c^\infty$ represented the diffusivity and bulk equilibrium solubility of the organic solute in the solution, respectively, and r was the particle radius. Bulk solubility of the organic solute increased exponentially with linear increase of solvent concentration. Therefore, with higher solvent concentration, nanoparticles grew faster to be out of the nano-range. It was suggested that solvent had to be removed from the suspension quickly by flash solvent evaporation (Kumar & Prud'homme (2009) *Chemical Engineering Science* 64 (6):1358-1361) or dialysis.

Effect of Drug Loading Rates. The dependence of particle size on DLR was measured by using PEG-b-PCL nanoparticles encapsulating β-carotene. It was observed that nanoparticle diameters increased with higher DLR. At higher DLR, β-carotene nucleation and growth were relatively faster compared to the polymer micellization. Before the polymer arrested the growth of the particles, they had more time to become bigger. With no drug encapsulated in the nanoparticles, it was found that the radius of the nanoparticles was 9 nm, which was consistent with the size of PEG-b-PCL micelles. It was of interest that the dependence of particle size on DLR was linear, which was consistent with the analysis of bifenthrin nanoparticles (Liu, et al. (2008) *Pest Management Science* 64 (8):808-812).

What is claimed is:

1. A nanohybrid drug delivery composition comprising
   a multivalent polymeric scaffold nanocore consisting of branched polyethyleneimine or poly(amidoamine) (PAMAM) dendrimer with a therapeutic agent and a targeting agent covalently attached thereto; and
   an outer shell encapsulating the polymeric scaffold nanocore, the therapeutic agent and the targeting agent, wherein the shell consists of poly-(lactic acid-co-glycolic acid), polyethylene glycol-b-polylactide-co-glycolide, polyethylene glycol-b-poly-L-lactic acid, or a unilamellar liposome consisting of 1,2-distearoyl-sn-glycero-3-phosphoethanolamine-N-mPEG-2000, 1,2-dioleoyl-sn-glycero-3-phosphocholine, 1,2-dioleoyl-sn-glycero-3-phospho-(1'-rac-glycerol) and cholesterol.

2. The drug delivery composition of claim 1, wherein the therapeutic agent comprises an anti-cancer agent, anti-angiogenic agent, or anti-viral agent.

3. The drug delivery composition of claim 1, wherein the targeting agent selectively targets a cancer cell or immune cell.

4. The drug delivery composition of claim 1, further comprising at least one imaging agent.

5. The drug delivery composition of claim 4, wherein the imaging agent is attached to the multivalent polymeric scaffold nanocore.

6. The drug delivery composition of claim 4, wherein the imaging agent is attached to the outer shell.

7. A pharmaceutical composition comprising the nanohybrid drug delivery composition of claim 1 and a pharmaceutically acceptable carrier.

8. A kit comprising the nanohybrid drug delivery composition of claim 1.

9. A method for preventing or treating a disease or condition comprising administering to a subject in need thereof an effective amount of the nanohybrid drug delivery composition of claim 1 to decrease one or more signs or symptoms of the disease or condition.

10. The nanohybrid drug delivery composition of claim 1 wherein the multivalent polymeric scaffold nanocore is a particle of no more than 15 nm in size and the shell encapsulating the polymeric scaffold nanocore is no more than 150 nm in size.

* * * * *